(12) United States Patent
D'Halluin

(10) Patent No.: US 9,574,201 B2
(45) Date of Patent: Feb. 21, 2017

(54) METHODS AND MEANS TO MODIFY A PLANT GENOME AT A NUCLEOTIDE SEQUENCE COMMONLY USED IN PLANT GENOME ENGINEERING

(75) Inventor: Kathleen D'Halluin, Mariakerke (BE)

(73) Assignee: Bayer CropScience NV, Diegem (BE)

( * ) Notice: Subject to any disclaimer, the term of this patent is extended or adjusted under 35 U.S.C. 154(b) by 902 days.

(21) Appl. No.: 13/700,773

(22) PCT Filed: Jun. 7, 2011

(86) PCT No.: PCT/EP2011/002895
§ 371 (c)(1),
(2), (4) Date: Jan. 16, 2013

(87) PCT Pub. No.: WO2011/154159
PCT Pub. Date: Dec. 15, 2011

(65) Prior Publication Data
US 2013/0145490 A1 Jun. 6, 2013

Related U.S. Application Data

(60) Provisional application No. 61/355,849, filed on Jun. 17, 2010.

(30) Foreign Application Priority Data

Jun. 9, 2010 (EP) .................................... 10005941

(51) Int. Cl.
*C12N 15/82* (2006.01)
*A01G 1/00* (2006.01)

(52) U.S. Cl.
CPC ........... *C12N 15/8213* (2013.01); *A01G 1/001* (2013.01)

(58) Field of Classification Search
None
See application file for complete search history.

(56) References Cited

U.S. PATENT DOCUMENTS

| | | |
|---|---|---|
| 2,031,826 A | 2/1936 | Ekstromer et al. |
| 4,761,373 A | 8/1988 | Anderson et al. |
| 4,962,028 A | 10/1990 | Bedbrook et al. |
| 5,013,659 A | 5/1991 | Bedbrook et al. |
| 5,141,870 A | 8/1992 | Bedbrook et al. |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,352,605 A | 10/1994 | Fraley et al. |
| 5,378,824 A | 1/1995 | Bedbrook et al. |
| 5,463,175 A | 10/1995 | Barry et al. |
| 5,504,200 A | 4/1996 | Hall et al. |
| 5,561,236 A | 10/1996 | Leemans et al. |
| 5,605,011 A | 2/1997 | Bedbrook et al. |
| 5,608,152 A | 3/1997 | Kridl et al. |
| 5,616,273 A | 4/1997 | Clark et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,776,760 A | 7/1998 | Barry et al. |
| 5,824,790 A | 10/1998 | Keeling et al. |
| 5,908,810 A | 6/1999 | Donn |
| 5,908,975 A | 6/1999 | Caimi et al. |
| 5,928,937 A | 7/1999 | Kakefuda et al. |
| 6,013,861 A | 1/2000 | Bird et al. |
| 6,130,367 A | 10/2000 | Kossmann et al. |
| 6,162,966 A | 12/2000 | Kossmann et al. |
| 6,207,880 B1 | 3/2001 | Kossmann et al. |
| 6,211,436 B1 | 4/2001 | Kossmann et al. |
| 6,245,968 B1 | 6/2001 | Boudec et al. |
| 6,255,561 B1 | 7/2001 | Kossman et al. |
| 6,255,563 B1 | 7/2001 | Emmermann et al. |
| 6,268,549 B1 | 7/2001 | Sailland et al. |
| 6,284,479 B1 | 9/2001 | Nichols |
| 6,307,124 B1 | 10/2001 | Kossmann et al. |
| 6,566,587 B1 | 5/2003 | Lebrun et al. |
| 6,590,141 B1 | 7/2003 | Frohberg |
| 6,699,694 B1 | 3/2004 | Buttcher et al. |
| 6,734,341 B2 | 5/2004 | Singletary et al. |
| 6,768,044 B1 | 7/2004 | Boudec et al. |

(Continued)

FOREIGN PATENT DOCUMENTS

| | | |
|---|---|---|
| EP | 04077624.7 | 9/2004 |
| EP | 06009836.5 | 5/2006 |

(Continued)

OTHER PUBLICATIONS

Grizot et al. "Generation of Redesigned Homing Endonucleases Comprising DNA-binding Domains Derived From Two Different Scaffolds" Nucleic Acids Research, Dec. 21, 2009, pp. 2006-2018, 2010, vol. 38, No. 6, doi:10.1093/nar/gkp1171.
Puchta, Holger "Repair of Genomic Double-Strand Breaks in Somatic Plant Cells by One-Sided Invasion of Homologous Sequences", The Plant Journal, 1998, pp. 331-339, vol. 13(3).
Wright et al. "High-Frequency Homologous Recombination in Plants Mediated by Zinc-Finger Nucleases", The Plant Journal, 2005, pp. 693-705, vol. 44, doi: 10.1111/j.1365-313X.2005.
An Y.Q. et al., Strong, constitutive expression of the Arabidopsis ACT2/ACT8 actin subclass in vegetative tissues, 1996, The Plant Journal, 10: 107-121.
An et al., Conserved Expression of the Arabidopsis ACT1 and ACT3 Actin Subclass in Organ Primordia and Mature Pollen, 1996, Plant Cell, 8: 15-30.
Arnould S. et al., Engineering of Large Numbers of Highly Specific Homing Endonucleases that Induce Recombination, 2006, Journal of Molecular Biology, 355 (3): 443-458.
Ausubel et al., Current Protocols in Molecular Biology, 1994, vol. 2.

(Continued)

*Primary Examiner* — Matthew Keogh

(57) ABSTRACT

Methods and means are provided to modify in a targeted manner the plant genome of transgenic plants comprising chimeric genes wherein the chimeric genes have a DNA element commonly used in plant molecular biology. Redesigned meganucleases to cleave such an element commonly used in plant molecular biology are provided.

10 Claims, 6 Drawing Sheets

(56) References Cited

U.S. PATENT DOCUMENTS

| | | |
|---|---|---|
| 6,791,010 B1 | 9/2004 | Frohberg |
| 6,794,558 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,951,969 B1 | 10/2005 | Loerz et al. |
| 7,112,665 B1 | 9/2006 | Leemans et al. |
| 7,399,621 B2 | 7/2008 | Hammer et al. |
| 7,405,347 B2 | 7/2008 | Hammer et al. |
| 7,488,866 B2 | 2/2009 | Hammer et al. |
| 7,504,561 B2 | 3/2009 | Hammer et al. |
| 7,534,937 B2 | 5/2009 | Hammer et al. |
| 7,538,262 B2 | 5/2009 | Hammer et al. |
| 7,659,376 B2 | 2/2010 | Hammer et al. |
| 7,674,958 B2 | 3/2010 | Peters et al. |
| 7,700,842 B2 | 4/2010 | Hammer |
| 7,807,881 B2 | 10/2010 | Hammer et al. |
| 7,834,249 B2 | 11/2010 | Schouten et al. |
| 7,910,805 B2 | 3/2011 | Duck et al. |
| 7,960,615 B2 | 6/2011 | Peters et al. |
| 7,960,616 B2 | 6/2011 | Heinrichs et al. |
| 7,989,679 B2 | 8/2011 | Koziel et al. |
| 8,003,854 B2 | 8/2011 | Peters et al. |
| 8,097,775 B2 | 1/2012 | Hammer et al. |
| 2001/0019975 A1 | 9/2001 | Uota |
| 2003/0167529 A1 | 9/2003 | Landschutze |
| 2004/0073966 A1 | 4/2004 | Zink et al. |
| 2005/0257283 A1 | 11/2005 | Matringe et al. |
| 2006/0015966 A1 | 1/2006 | Landschutze |
| 2006/0168690 A1 | 7/2006 | Shibatani et al. |
| 2007/0117128 A1* | 5/2007 | Smith ............ C12N 9/22 435/6.12 |
| 2007/0169218 A1 | 7/2007 | Carr et al. |
| 2007/0289035 A1 | 12/2007 | Vande Berg et al. |
| 2007/0295251 A1 | 12/2007 | Heinrichs |
| 2008/0025033 A1 | 1/2008 | De Groot |
| 2009/0293155 A1* | 11/2009 | Paul ............ C12N 15/8213 800/288 |

FOREIGN PATENT DOCUMENTS

| | | |
|---|---|---|
| EP | 1999263 | 12/2008 |
| WO | 84/02913 | 8/1984 |
| WO | 89/10396 | 11/1989 |
| WO | 9102071 | 2/1991 |
| WO | 91/13980 | 9/1991 |
| WO | 92/13956 | 8/1992 |
| WO | 92/14827 | 9/1992 |
| WO | 94/04692 | 3/1994 |
| WO | 94/04693 | 3/1994 |
| WO | 94/09144 | 4/1994 |
| WO | 94/11520 | 5/1994 |
| WO | 94/18313 | 8/1994 |
| WO | 94/21795 | 9/1994 |
| WO | 95/04826 | 2/1995 |
| WO | 95/06128 | 3/1995 |
| WO | 95/07355 | 3/1995 |
| WO | 95/09233 | 4/1995 |
| WO | 95/13389 | 5/1995 |
| WO | 95/26407 | 10/1995 |
| WO | 95/31553 | 11/1995 |
| WO | 95/35026 | 12/1995 |
| WO | 96/01904 | 1/1996 |
| WO | 96/06932 | 3/1996 |
| WO | 96/14408 | 5/1996 |
| WO | 96/19581 | 6/1996 |
| WO | 96/21023 | 7/1996 |
| WO | 96/33270 | 10/1996 |
| WO | 96/34968 | 11/1996 |
| WO | 97/13865 | 4/1997 |
| WO | 97/20936 | 6/1997 |
| WO | 97/45545 | 12/1997 |
| WO | 97/47806 | 12/1997 |
| WO | 97/47807 | 12/1997 |
| WO | 97/47808 | 12/1997 |
| WO | 98/20145 | 5/1998 |
| WO | 98/22604 | 5/1998 |
| WO | 98/27212 | 6/1998 |
| WO | 98/32326 | 7/1998 |
| WO | 98/39460 | 9/1998 |
| WO | 98/40503 | 9/1998 |
| WO | 98/45461 | 10/1998 |
| WO | 99/12950 | 3/1999 |
| WO | 9920776 | 4/1999 |
| WO | 99/24593 | 5/1999 |
| WO | 99/53072 | 10/1999 |
| WO | 99/66050 | 12/1999 |
| WO | 00/04173 | 1/2000 |
| WO | 00/11192 | 3/2000 |
| WO | 00/14249 | 3/2000 |
| WO | 00/28052 | 5/2000 |
| WO | 0037663 A1 | 6/2000 |
| WO | 00/46386 | 8/2000 |
| WO | 00/47727 | 8/2000 |
| WO | 00/66746 | 11/2000 |
| WO | 00/66747 | 11/2000 |
| WO | 00/73422 | 12/2000 |
| WO | 00/77229 | 12/2000 |
| WO | 01/14569 | 3/2001 |
| WO | 01/19975 | 3/2001 |
| WO | 01/24615 | 4/2001 |
| WO | 01/41558 | 6/2001 |
| WO | 01/66704 | 9/2001 |
| WO | 01/83818 | 11/2001 |
| WO | 01/98509 | 12/2001 |
| WO | 02/26995 | 4/2002 |
| WO | 02/34923 | 5/2002 |
| WO | 02/36782 | 5/2002 |
| WO | 02/46387 | 6/2002 |
| WO | 02/079410 | 10/2002 |
| WO | 02/101059 | 12/2002 |
| WO | 03/013224 | 2/2003 |
| WO | 03/013226 | 2/2003 |
| WO | 03/033540 | 4/2003 |
| WO | 03/071860 | 9/2003 |
| WO | 03/080809 | 10/2003 |
| WO | 03/092360 | 11/2003 |
| WO | 2004/040012 | 5/2004 |
| WO | 2004/056999 | 7/2004 |
| WO | 2004/067736 | 8/2004 |
| WO | 2004/078983 | 9/2004 |
| WO | 2004/090140 | 10/2004 |
| WO | 2004/106529 | 12/2004 |
| WO | 2005/002359 | 1/2005 |
| WO | 2005/012515 | 2/2005 |
| WO | 2005/020673 | 3/2005 |
| WO | 2005/030941 | 4/2005 |
| WO | 2005/030942 | 4/2005 |
| WO | 2005/093093 | 10/2005 |
| WO | 2005/095617 | 10/2005 |
| WO | 2005/095618 | 10/2005 |
| WO | 2005/095619 | 10/2005 |
| WO | 2005/095632 | 10/2005 |
| WO | 2005/123927 | 12/2005 |
| WO | 2006/007373 | 1/2006 |
| WO | 2006/015376 | 2/2006 |
| WO | 2006/018319 | 2/2006 |
| WO | 2006/024351 | 3/2006 |
| WO | 2006/032538 | 3/2006 |
| WO | 2006/045633 | 5/2006 |
| WO | 2006/060634 | 6/2006 |
| WO | 2006/063862 | 6/2006 |
| WO | 2006/072603 | 7/2006 |
| WO | 2006/103107 | 10/2006 |
| WO | 2006/105946 | 10/2006 |
| WO | 2006/108702 | 10/2006 |
| WO | 2006/129204 | 12/2006 |
| WO | 2006/133827 | 12/2006 |
| WO | 2007/009823 | 1/2007 |
| WO | 2007/024782 | 3/2007 |
| WO | 2007/027777 | 3/2007 |
| WO | 2007/035650 | 3/2007 |
| WO | 2007/039314 | 4/2007 |

(56) References Cited

FOREIGN PATENT DOCUMENTS

| WO | 2007/039316 | 4/2007 |
|---|---|---|
| WO | 2007/047859 | 4/2007 |
| WO | 2007/049095 | 5/2007 |
| WO | 2007/049156 | 5/2007 |
| WO | 2007/074405 | 7/2007 |
| WO | 2007/080126 | 7/2007 |
| WO | 2007/080127 | 7/2007 |
| WO | 2007/093836 | 8/2007 |
| WO | 2007/103567 | 9/2007 |
| WO | 2007/107302 | 9/2007 |
| WO | 2007/107326 | 9/2007 |
| WO | 2008/017518 | 2/2008 |
| WO | 2008/037436 | 4/2008 |
| WO | 2008/080630 | 7/2008 |
| WO | 2008/080631 | 7/2008 |
| WO | 2008/090008 | 7/2008 |
| WO | 2008/102199 | 8/2008 |
| WO | 2008/122406 | 10/2008 |
| WO | 2008/148559 | 12/2008 |
| WO | 2008/150473 | 12/2008 |
| WO | 2008/151780 | 12/2008 |
| WO | 2009/114321 | 9/2009 |
| WO | 2009/144079 | 12/2009 |
| WO | 2009/149787 | 12/2009 |

OTHER PUBLICATIONS

Baumlein et al., A novel seed protein gene from Vicia faba is developmentally regulated in transgenic tobacco and Arabidopsis plants, 1991, Mol. Gen. Genet., 225(3): 459-67.
Beck et al., Gene: an international journal focusing on gene cloning and gene structure and function, 1982, Gene 19(3): 327-336.
Benfey et al., 1989, The CaMV 35S enhancer contains at least two domains which can confer different developmental and tissue-specific expression patterns, 1989, EMBO J., 8: 2195-2202.
Bustos et al., Regulation of β-Glucuronidase Expression in Transgenic Tobacco Plants by an A/T-Rich, cis-Acting Sequence Found Upstream of a French Bean β-Phaseolin Gene, 1989, Plant Cell 1, 9: 839-53.
Carrington J. et al., Cap-Independent Enhancement of Translation by a Plant Potyvirus 5' Nontranslated Region, 1990, J. Virol, 64(4): 1590-1597.
Chaboute M. et al., Genomic organization and nucleotide sequences of two histone H3 and two histone, 1987, Plant Mol, Biol., 8: 179-191.
Chilton and Que, Targeted Integration of T-DNA into the Tobacco Genome at Double-Stranded Breaks: New Insights on the Mechanism of T-DNA Integration, 2003, Plant Physiol, 133:956-965.
Christensen et al., Maize Polyubiquitin genes: structure, thermal perturbation of expression and transcript slicing, and promoter activity following transfer to protoplasts by electroporation, 1992, Plant Mol. Biol., 18:675.
Comai et al., An Altered aroA Gene Product Confers Resistance to the Herbicide Glyphosate, 1983, Science, 221: 370-371.
Crickmore et al., Revision of the Nomenclature for the Bacillus thuringiensis Pesticidal Crystal Proteins, 1998, Microbiology and Molecular Biology Reviews, 62: 807-813.
Depicker A. et al., Nopaline Synthase: Transcript Mapping and DNA Sequence, 1982, Journal of Molecular and Applied Genetics, 1: 561-573.
De Greve H. et al., Nucleotide Sequence and Transcript Map of the Agrobacterium tumefaciens Ti Plasmid-Encoded Octopine Synthase Gene, 1982, Journal of Malecular and Applied Genetics, 1: 499-511.
D'Haese et al., Identification of sequences involved in the polyadenylation of higher plant nuclear transcripts using Agrobacterium T-DNA genes as models, D1983, The EMBO Journal, 2: 419-426.
D'Halluin et al., Homologous recombination: a basis for targeted genome optimization in crop species such as maize, 2008, Plant Biotechnol, J. 6: 93-102.

Eckes et al., Isolation and characterization of a light-inducible, organ-specific gene from potato and analysis of its expression after tagging and transfer into tobacco and potato shoots, 1986, Mol. Gen. Genet., 205: 14-22.
Gao Huirong et al., Heritable targeted mutagenesis in maize using a designed endonuclease, 2010, The Plant Journal, 61(1): 176-187.
Gasser et al., Structure, Expression, and Evolution of the 5-Enolpyruvylshikimate-3phosphate Synthase Genes of Petunia and Tomato, 1988, J. Biol. Chem., 263: 4280-4289.
Harpster et al., Relative strengths of the 35S califlower mosaic virus, 1', 2', and nopaline synthase promoters in transformed tobacco sugarbeet and oilseed rape callus tissue, 1988, Mol. Gen. Genet, 212: 182-190.
Holtorf et al., Comparison of different constitutive and inducible promoters for the overexpression of transgenes in Arabidopsis thaliana, 1995, Plant Mol. Biol., 29: 637-649.
Hudspeth et al., Structure and expression of the maize gene encoding the phosphoenolpyruvate carboxylase isozyme involved in C4 photosynthesis, 1989, Plant Mot Biol., 12: 579-589.
Isalan et al., A rapid, generally applicable method to engineer zinc fingers illustrated by targeting the HIV-1 promoter, 2001, Nature Biotechnology 19: 656-660.
Joseffson et al., Structure of a Gene Encodingt he 1.7 S Storage Protein, Napin, from Brassica napus, 1987, J. Biol. Chem., 262: 12196-12201.
Kalderon et al., A Short Amino Acid Sequence Able to Specify Nuclear Location, 1984, Cell, 39: 499-509.
Kaster et al., Analysis of a bacterial hygromycin B resistance gene by twraniptional and translational fusions and by DNA sequencing, 1983, NAR, 11: 6895-6911.
Keil et al., Both wound-inducible and tuber-specific expression are mediated by the promoter of a single member of the potato proteinase inhibitor 11 gene family, 1989, EMBO J. 8(5): 1323-1330.
Keller et al., Glycine-rich cell wall proteins in bean: gene structure and association of the protein with the vascular system, 1988, EMBO J. 7, 12: 3625-3633.
Keller et al., specific expression of a novel cell wall hydroxyproline-rich glycoprotein gene in lateral root initiation, 1989, Genes Dev., 3: 1639-1646.
Krebbers et al., Four genes in two diverged subfamilies encode the ribulose-I,5-bisphosphate carboxylase small subunit polypeptides of Arabidopsis thaliana, 1988, Plant Molecular Biology, 11: 745-759.
Kumar and Fladung, Controlling transgene integration in plants,2001, Trends in Plant Science, 6: 155-159.
Liu et al., Design of polydactyl zinc-finger proteins for unique addressing within complex genomes, 1997, Proc. Natl. Acad. Sci. USA 94: 5525-5530.
McElroy D. et al., Isolation of an Efficient Actin Promoter for Use in Rice Transformation, 1990, The Plant Cell, 2: 163-171.
Moellenbeck et al., Insecticidal proteins from Bacillus thuringiensis protect corn from corn rootworms, 2001, Nat. Biotechnol., 19: 668-72.
Needleman and Wunsch, A General Method Applicable to the Search for Similarities in the Amino Acid Sequence of Two Proteins, 1970, Mol. Biol. (1970) 48, 443-453.
Odell et al., Identification of DNA sequences required for activity of the cauliflower mosaic virus 35S promoter, 1985, Nature, 313: 810-812.
Peleman et al., Structure and expression analyses of the S-adenosylmethionine synthetase gene family in Arabidopsis thaliana, 1989, Gene 84: 359-369.
Puchta et al., 1996, Two different but related mechanisms are used in plants for the repair of genomic double-strand breaks by homologous recombination, Proc. Natl. Acad. Sci. U.S.A., 93: 5055-5060.
Raikhel, Nuclear Targeting in Plants, 1992, Plant Physiol, 100: 1627-1632.
Richins R.D. et al., Sequence of figwort mosaic virus DNA (caulimovirus group), 1987, Nucleic Acids Research, 15: 8451-8455.
Sambrook et al., 1989, Molecular Cloning: A Laboratory Manual, Second Edition, Cold Spring Harbour.

(56) References Cited

OTHER PUBLICATIONS

Sanfacon et al., A dissection of the cauliflower mosaic virus polyadenylation signal, 1991, Genes Dev., 5: 141.
Schnepf et al., Characterization of Cry34/Cry35 Binary Insecticidal Proteins from Diverse Bacillus thuringiensis Strain Collections, 2006, Applied Environm. Microbiol., 71: 1765-1774.
Seligman L.M. et al., Mutations altering the cleavage specificity of a homing endonuclease, 2002, Nucleic Acids Research, 30(17): 3870-3879.
Shah et al., Engineering Herbicide Tolerance in Transgenic Plants, 1986, Science, 233: 478-481.
Shirsat et al., Sequences responsible for the tissue specific promoter activity of a pea legumin gene in tobacco, 1989, Mol. Gen. Genet., 215(2): 326-331.
Stalberg et al., Disruption of an overlapping E-box/ABRE motif abolished high transcription of the napA storage-protein promoter in transgenic Brassica napus seeds, 1996, Planta, 199: 515-519.
Sussman D. et al., Isolation and Characterization of New Homing Endonuclease Specificities at Individual Target Site Positions, 2004, Journal of Molecular Biology, 342(1): 31-41.
Thompson et al., Characterization of the herbicide-resistance gene bar from Streptomyces hygroscopicus, 1992, Gene, 119: 247-251.
Thompson C. et al., Cleavage and recognition pattern of a double-strand-specific endonuclease (I-Cre1 I) encoded by the chloroplast 23s rRNA intron of Chlamydomonas reinhardtii, 1987, The EMBO Journal, 6: 2519-2523.
Tranel and Wright, Resistance of weeds to ALS-inhibiting herbicides: what have we learned? 2002, Weed Science, 50: 700-712.
Verdaguer et al., Isolation and expression in transgenic tobacco and rice plants, of the cassava vein mosaic virus (CVMV) promoter, 1996, Plant Mol. Biol., 31: 1129.
Verdaguer et al., Functional organization of the cassava vein mosaic virus (CsVMV), 1998, Plant Mol. Biol., 37: 1055.
Wehrkam & Richter S. et al., Characterisation of a new reporter system allowing high throughput in planta screening for recombination events before and after controlled DNA double strand break induction, 2009, Plant Physiology and Biochemistry, 47(4), 248-255.
Wohlleben W. et al., Nucleotide sequence of the phosphoinothricin N-acetyltransferase gene from Streptomyces viridochromogenes Tn494 and its expression in Nicotiana tabacum, 1988, Gene, 70(1): 25-37.
NCBI Accession No. V00618, Thompson, C.J. et al., Streptomyces hygroscopicus bar gene conferring resistance to herbicide bialaphos, X05822, EMBO J. 6 (9), 2519-2523 (1987).
NCBI Accession No. X05822, Beck, E., et al., Transposon Tn5 fragment encoding neomycin and kanamycin resistance (neo) and a fragment of the reading frame of a further protein, V00618, J01834, gENE 19 (3), 327-336 (1982).
International Search Report and Written Opinion for PCT/EP2011/002895, mailed Jul. 6, 2011.

* cited by examiner

```
Met Ala Pro Lys Lys Lys Arg Lys Val His Met Asn Thr Lys Tyr Asn
1               5                   10                  15
Lys Lys Phe Leu Leu Tyr Leu Ala Gly Phe Val Asp Gly Asp Gly Ser
            20                  25                  30
Ile Ile Ala Ser Ile Ser Pro Asn Gln Ser Arg Lys Phe Lys His Gln
        35                  40                  45
Leu Arg Leu Thr Phe Thr Val Thr Gln Lys Thr Gln Arg Arg Trp Phe
    50                  55                  60
Leu Asp Lys Leu Val Asp Lys Ile Gly Val Gly Lys Val Arg Asp Arg
65                  70                  75                  80
Gly Ser Val Ser Asp Tyr Arg Leu Ser Gln Ile Lys Pro Leu His Asn
            85                  90                  95
Phe Leu Thr Gln Leu Gln Pro Phe Leu Lys Leu Lys Gln Lys Gln Ala
        100                 105                 110
Asn Leu Val Leu Lys Ile Ile Glu Gln Leu Pro Ser Ala Lys Glu Ser
    115                 120                 125
Pro Asp Lys Phe Leu Glu Val Cys Thr Trp Val Asp Gln Ile Ala Ala
130                 135                 140
Leu Asn Asp Ser Lys Thr Arg Lys Thr Ser Glu Thr Val Arg Ala
145                 150                 155                 160
Val Leu Asp Ser Leu Ser Glu Lys Lys Lys Ser Ser Pro
            165                 170
```

Figure 2

Met Ala Pro Lys Lys Lys Arg Lys Val His Met Asn Thr Lys Tyr Asn
1               5                   10                  15
Glu Glu Phe Leu Leu Tyr Leu Ala Gly Phe Val Asp Gly Asp Gly Ser
            20                  25                  30
Ile Ile Ala Ser Ile Ser Pro Arg Gln Ser Tyr Lys Phe Lys His Glu
        35                  40                  45
Leu Arg Leu Thr Phe Gln Val Thr Gln Lys Thr Gln Arg Arg Trp Phe
50                  55                  60
Leu Asp Glu Leu Val Asp Glu Ile Gly Val Gly Lys Val Arg Asp Arg
65                  70                  75                  80
Gly Ser Val Ser Asp Tyr Arg Leu Ser Gln Ile Lys Pro Leu His Asn
            85                  90                  95
Phe Leu Thr Gln Leu Gln Pro Phe Leu Glu Leu Lys Gln Lys Gln Ala
            100                 105                 110
Asn Leu Val Leu Lys Ile Ile Glu Gln Leu Pro Ser Ala Lys Glu Ser
            115                 120                 125
Pro Asp Lys Phe Leu Glu Val Cys Thr Trp Val Asp Gln Ile Ala Ala
            130                 135                 140
Leu Asn Asp Ser Lys Thr Arg Lys Thr Ser Glu Thr Val Arg Ala
145                 150                 155                 160
Val Leu Asp Ser Leu Ser Glu Lys Lys Lys Lys Ser Ser Pro
                165                 170

Figure 3

```
Met Ala Lys Pro Pro Lys Lys Lys Arg Lys Val His Met Asn Thr Lys
1               5                   10                  15
Tyr Asn Lys Glu Phe Leu Leu Tyr Leu Ala Gly Phe Val Asp Gly Asp
                20                  25                  30
Gly Ser Ile Ile Ala Ser Ile Ser Pro Arg Gln Ser Tyr Lys Phe Lys
            35                  40                  45
His Glu Leu Arg Leu Thr Phe Gln Val Thr Gln Lys Thr Gln Arg Arg
        50                  55                  60
Trp Phe Leu Asp Lys Leu Val Asp Glu Ile Gly Val Gly Lys Val Arg
65                  70                  75                  80
Asp Arg Gly Ser Val Ser Asp Tyr Arg Leu Ser Gln Ile Lys Pro Leu
                85                  90                  95
His Asn Phe Leu Thr Gln Leu Gln Pro Phe Leu Lys Leu Lys Gln Lys
            100                 105                 110
Gln Ala Asn Leu Val Leu Lys Ile Glu Gln Leu Pro Ser Ala Lys
        115                 120                 125
Glu Ser Pro Asp Lys Phe Leu Glu Val Cys Thr Trp Val Asp Gln Ile
        130                 135                 140
Ala Ala Leu Asn Asp Ser Lys Thr Arg Lys Thr Thr Ser Glu Thr Val
145                 150                 155                 160
Arg Ala Val Leu Asp Ser Leu Pro Gly Ser Val Gly Gly Leu Ser Pro
                165                 170                 175
Ser Gln Ala Ser Ser Ala Ala Ser Ser Ser Ser Ser Pro Gly Ser
            180                 185                 190
```

Figure 4

```
Gly Ile Ser Glu Ala Leu Arg Ala Gly Ala Thr Lys Ser Lys Glu Phe
            195                 200                 205
Leu Tyr Leu Ala Gly Phe Val Asp Gly Asp Gly Ser Ile Ile Ala
        210                 215                 220
Ser Ile Ser Pro Asn Gln Ser Arg Lys Phe Lys His Gln Leu Arg Leu
225                 230                 235                 240
Thr Phe Thr Val Thr Gln Lys Thr Gln Arg Arg Trp Phe Leu Asp Lys
            245                 250                 255
Leu Val Asp Glu Ile Gly Val Gly Lys Val Arg Asp Arg Gly Ser Val
        260                 265                 270
Ser Asp Tyr Arg Leu Ser Gln Ile Lys Lys Pro Leu His Asn Phe Leu Thr
275                 280                 285
Gln Leu Gln Pro Phe Leu Lys Leu Lys Gln Lys Gln Ala Asn Leu Val
        290                 295                 300
Leu Lys Ile Ile Glu Gln Leu Pro Ser Ala Lys Glu Ser Pro Asp Lys
305                 310                 315                 320
Phe Leu Glu Val Cys Thr Trp Val Asp Gln Ile Ala Ala Leu Asn Asp
            325                 330                 335
Ser Lys Thr Arg Lys Thr Thr Ser Glu Thr Val Arg Ala Val Leu Asp
        340                 345                 350
Ser Leu Ser Glu Lys Lys Lys Ser Ser Pro
355                 360
```

Figure 4 (cont'ed)

1. cggtcaacttccgtaccgagccgcaggaaccgcaggagtggacggacctcgtccgtctgcgggac
2. cggtcaacttccgtaccgagccgcaggaaccgcaggagtggacggacctcgtccgtctgcgggac
3. cggtcaacttccgtaccgagccgcaggaaccgcaggagtggacg-acgacctcgtccgtctgcgggac
4. cggtcaacttc------------------------------------cgtccgtctgcgggac
5. cggtcaacttccgtaccgagccgcaggaaccgcaggagtg------gacctcgtccgtctgcgggac
6. cggtcaacttccgtaccgagccgcaggaac-----------------cctcgtccgtctgcgggac
7. cggtcaacttccgtaccgagccgcagga--------------------acctcgtccgtctgcgggac
8. cggtcaacttccgtaccgagccgcaggaaccgc--------------acgacctcgtccgtctgcgggac
9. cggtcaacttccgtaccgagccgcaggaaccgcaggagtggacgacgacctcgtccgtctgcgggac

a

Figure 5

METHODS AND MEANS TO MODIFY A PLANT GENOME AT A NUCLEOTIDE SEQUENCE COMMONLY USED IN PLANT GENOME ENGINEERING

CROSS-REFERENCE TO RELATED APPLICATIONS

This application is a §371 U.S. National Stage of International Application No. PCT/EP2011/002895, filed Jun. 7, 2011, which claims the benefit of European Patent Application Serial No. 10005941.9, filed Jun. 9, 2010 and U.S. Patent Application Ser. No. 61/355,849, filed Jun. 17, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS10-2010-WO1.ST25.txt", created on Oct. 22, 2012, and having a size of 17,000 bytes and is filed concurrently with the specification. A replacement sequence listing is submitted on May 9, 2013 as an ASCII formatted sequence listing with the file named "BCS10-2010-WO1v2.ST25.txt" which was created on May 8, 2013 and has a file size of 35,000 bytes. This replacement sequence listing is identical to the sequence listing that was filed on Jun. 7, 2011 in the corresponding PCT International Application No. PCT/EP11/002895. The sequence listing contained in this ASCII formatted document is part of the specification and is herein incorporated by reference in its entirety.

FIELD OF THE INVENTION

The invention relates to the field of agronomy. More particularly, the invention provides methods and means to introduce a targeted modification, including insertion, deletion or substitution, at a precisely localized nucleotide sequence in the genome of a transgenic plant, wherein the nucleotide sequence is comprised within an element or DNA fragment frequently used in plant transgenesis, such as a commonly used selectable marker gene. The modifications are triggered in a first step by induction of a double stranded break at the recognition nucleotide sequence using meganucleases derived from naturally occurring meganucleases which have been re-designed to recognize the recognition site and cleave it.

BACKGROUND ART

The need to introduce targeted modifications in plant genomes, including the control over the location of integration of foreign DNA in plants has become increasingly important, and several methods have been developed in an effort to meet this need (for a review see Kumar and Fladung, 2001, *Trends in Plant Science*, 6, pp 155-159). These methods mostly rely on the initial introduction of a double stranded DNA break at the targeted location.

Activation of the target locus and/or repair or donor DNA through the induction of double stranded DNA breaks via rare-cutting endonucleases, such as I-SceI. has been shown to increase the frequency of homologous recombination by several orders of magnitude. (Puchta et al., 1996, *Proc. Natl. Acad. Sci. U.S.A.*, 93, pp 5055-5060; Chilton and Que, *Plant Physiol.*, 2003; D'Halluin et al. 2008 *Plant Biotechnol. J.* 6, 93-102).

WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through an I-SceI induced double strand break. Also disclosed are methods of treating or prophylaxis of a genetic disease in an individual in need thereof. Further disclosed are chimeric restriction endonucleases.

In addition, methods have been described which allow the design of rare cleaving endonucleases to alter substrate or sequence-specificity of the enzymes, thus allowing to induce a double stranded break at a locus of interest without being dependent on the presence of a recognition site for any of the natural rare-cleaving endonucleases. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci. USA* 94, 5525-5530). Another way of producing custom-made meganucleases, by selection from a library of variants, is described in WO2004/067736. Custom made meganucleases or redesigned meganucleases with altered sequence specificity and DNA-binding affinity may also be obtained through rational design as described in WO2007/047859.

WO2007/049095 describes "LADGLIDADG" homing endonuclease variants having mutations in two separate subdomains, each binding a distinct part of a modified DNA target half site, such that the endonuclease variant is able to cleave a chimeric DNA target sequence comprising the nucleotides bound by each subdomain.

WO2007/049156 and WO2007/093836 describe I-CreI homing endonuclease variants having novel cleavage specificity and uses thereof.

WO2007/047859 describes rationally designed meganucleases with altered sequence specificity and DNA binding affinity.

WO2006/105946 described a method for the exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step, employing the therein described method for the removal of a selected DNA by microspore specific expression of a double stranded break inducing rare cleaving endonuclease.

U.S. provisional patent application 60/828,042 and European patent application 06020370.0, and WO2008/037436 describe variants of the methods and means of WO2006/105946 wherein the removal step of a selected DNA fragment induced by a double stranded break inducing rare cleaving endonuclease is under control of a germline-specific promoter. Other embodiments of the method relied on non-homologous endjoining at one end of the repair DNA and homologous recombination at the other end.

Gao et al. 2009, *The Plant Journal*, pp 1-11 describe heritable targeted mutagenesis in maize using a re-designed endonuclease.

Since the re-designed meganucleases are derived from naturally occurring endonucleases, the available potential recognition sites are not entirely random but appear to have some degree of resemblance to the nucleotide sequence originally recognized by the naturally occurring endonuclease upon which the re-designed meganuclease is based. As stated by Gao et al, 2009 (supra) the structure-based protein design method to modify the DNA-binding characteristics of I-CreI are based on visual inspection of the I-CreI-DNA co-crystal structure leading to a prediction of a large number of amino acid substitutions that change I-CreI base preference at particular positions in its recognition site. Individual amino acid substitutions were evaluated experimentally, and those that conferred the desired change in base preference were added to a database of mutations that can be "mixed and matched" to generate derivatives of I-CreI that recognize highly divergent DNA sites. In theory, the combinatorial diversity available using the current mutation database is sufficient to target an engineered endonuclease approximately every 1000 bp in a random DNA sequence.

Accordingly, there still remains a need for functional re-designed meganucleases which can recognize a recognition site in an DNA element or region previously introduced into a transgenic plant as a commonly used part of a transgene, and induce a double branded DNA break in that region with sufficient efficiency, thereby triggering the events required for e.g. insertion of foreign DNA, deletion or substitution by homologous recombination or non-homologous endjoining at the double stranded break site. Identification of such a pair of recognition site and re-designed meganuclease, enhances the available tools to modify a plant genome in a targeted manner, by allowing insertion, deletion or substitution of the DNA in the vicinity of the induced double stranded DNA break at the location of a previously introduced transgene, without having to resort to presence of historically introduced recognition sites for rare-cleaving endonucleases such as e.g. I-SceI (which does not occur naturally in plant cells).

These and other problems are solved as described hereinafter in the different detailed embodiments of the invention, as well as in the claims.

SUMMARY OF THE INVENTION

In one embodiment of the invention, a method is provided for introducing a foreign DNA molecule at a predefined site in a genome of a transgenic plant cell comprising the steps of
  a. inducing a double stranded DNA break at the pre-defined site;
  b. introducing the foreign DNA molecule in the plant cell;
  c. selecting a plant cell wherein the foreign DNA is introduced at the predefined site; and
  d. optionally regenerating the plant cell into a plant
characterized in that the predefined site is a nucleotide sequence different from a recognition site for a natural occurring meganuclease and that the predefined site is a nucleotide sequence commonly introduced as part of a transgene in a transgenic plant and wherein double stranded DNA break is induced by introduction of a non-naturally occurring single chain meganuclease or a pair of non-naturally occurring meganucleases which recognizes or recognize in concert the predefined site and induces or induce the double stranded break.

In another embodiment the invention provides a method for introducing a foreign DNA molecule at a predefined site in a genome of a plant cell comprising the steps of
  a. inducing a double stranded DNA break at the pre-defined site;
  b. introducing the foreign DNA molecule in the plant cell;
  c. selecting a plant cell wherein the foreign DNA is introduced at the predefined site; and
  d. optionally regenerating the plant cell into a plant
characterized in that the predefined site is comprised within a phosphinotricin acetyl transferase coding region from *S. hygroscopicus* (bar coding region), which may have the nucleotide sequence of SEQ ID No 3 and that the double stranded DNA break is induced by introduction of a single chain meganuclease or a pair of meganucleases which recognizes or recognize in concert the predefined site and induces or induce the double stranded break. The predefined site may comprise the nucleotide sequence of SEQ ID No 1 or SEQ ID No 2.

In yet another embodiment, a method is provided for introducing a foreign DNA molecule at a predefined site in a genome of a plant cell comprising the steps of
  a. inducing a double stranded DNA break at the pre-defined site;
  b. introducing the foreign DNA molecule in the plant cell;
  c. selecting a plant cell wherein the foreign DNA is introduced at the predefined site;
  d. optionally regenerating the plant cell into a plant
characterized in that the predefined site comprises the nucleotide sequence of SEQ ID No 1 or SEQ ID No. 2 and that the double stranded DNA break is induced by introduction of a single chain meganuclease or a pair of meganucleases which recognizes or recognize in concert the predefined site and induces or induce the double stranded break such as a meganuclease or the pair of meganucleases is/are derived from I-CreI (represented by SEQ ID No. 16) and wherein the following amino acids are present in one of the subunits: —S at position 32; Y at position 33; E at position 38; R at position 40; K at position 66; Q at position 80; T at position 42; R at position 77; R at position 68; R at position 70; Q at position 44; I at position 24; S at position 26; S at position 28 and R at position 30 or R at position 70; T at position 44; I at position 24; S at position 26; S at position 28; N at position 30; S at position 32; R at position 33; Q at position 38; Q at position 80; R at position 40; K at position 66; T at position 42; R at position 77 and R at position 68 (positions corresponding to I-Cre-I amino acid sequence). Examples of such meganuclease are proteins comprising the amino acid sequence of SEQ ID No. 5 and SEQ ID 6, respectively, encoded by a nucleic acid comprising the nucleotide sequence of SEQ ID No. 4 from nucleotide position 2004 to nucleotide position 2525 or to 2522, or the nucleotide sequence of SEQ ID No. 4 from nucleotide position 4885 to nucleotide position 5405 or to 5403. A single chain meganucleases according to the invention can be a protein comprising the amino acid sequence of SEQ ID No. 18, encoded by a nucleotide sequence comprising the nucleotide sequence of SEQ ID No. 17 from nucleotide position 1267 to 1605 and 1795 to 2541, or a protein comprising the amino acid sequence of SEQ ID No. 18 from amino acid position 1 to 167 and 208 to 362, encoded by a nucleotide sequence comprising the nucleotide sequence of SEQ ID No. 17 from nucleotide position 1267 to 1605, 1795 to 1956 and 2071 to 2541.

In any of the embodiments, the foreign DNA may be comprised within a repair DNA, the repair DNA comprising at least one flanking nucleotide sequence homologous to the upstream or downstream sequence of the nucleotide sequence of SEQ ID No. 1 or SEQ ID No. 2. The foreign DNA may comprises a selectable marker gene and/or a plant expressible gene of interest such as of a herbicide tolerance gene, an insect resistance gene, a disease resistance gene, an abiotic stress resistance gene, a enzyme involved in oil biosynthesis, carbohydrate biosynthesis, a enzyme involved in fiber strength or fiber length, an enzyme involved in biosynthesis of secondary metabolites. The foreign DNA may also be integrated as such, i.e. without flanking sequences with homology to the region around the pre-defined target site (without any further DNA), for integration by non-homologous end-joining The meganuclease or the pair of meganucleases may be expressed from a chimeric gene or a pair of chimeric genes, each comprising a plant expressible promoter operably linked to a coding region encoding the meganuclease or one of the pair of meganucleases, and further operationally linked to a DNA region involved in transcription termination and polyadenylation functional in a plant cell.

The invention further provides, plant cells and plants and seeds or propagating parts wherein the foreign DNA has been introduced into the predefined site, which have been obtained by the methods herein provided.

The invention also provides a method of growing a plant wherein the foreign DNA has been introduced into the predefined site, which has been obtained by the methods herein provided comprising the step of applying a chemical to the plant or substrate wherein the plant is grown.

Yet another embodiment of the invention concerns a process for producing a plant comprising foreign DNA integrated at the bar coding region comprising the step of crossing a plant consisting essentially of the plant cells obtained by the methods of the invention with another plant or with itself and optionally harvesting seeds.

The invention also concerns a process comprising the step of applying a chemical compound on a plant or a seed of a plant wherein the foreign DNA has been introduced into the predefined site, which has been obtained by the methods herein provided.

Another embodiment of the invention relates to the use of a meganuclease or a pair of meganucleases as herein described to introduce a foreign DNA into the bar coding region in a plant cell.

Yet another embodiment of the invention relates to the use of a custom made meganuclease to introduce a foreign DNA of interest at a predefined site in a plant cell.

BRIEF DESCRIPTION OF THE DRAWINGS

FIG. 2: Amino acid sequence of BAY 39/40 monomeric unit 2 ("40") (SEQ ID NO:4) (note that the amino acid sequence comprises a SV40 nuclear localization signal (amino acids 1 to 10)).

FIG. 3: Amino acid sequence of BAY 39/40 monomeric unit 1 ("39") (SEQ ID NO:5) (note that the amino acid sequence comprises an SV40 nuclear localization signal (amino acids 1 to 10)).

FIG. 4: Amino acid sequence of the single chain BAY 39/40 meganuclease (SEQ ID NO:18) (note that the amino acid sequence comprises an SV40 nuclear localization signal (amino acids 1-12) and a linker region (amino acids 168 to 205)).

FIG. 5: Alignment of the nucleotide sequence of PCR amplicons around the recognition site of the bar coding regions, in phosphinotricin sensitive lines derived from a transgenic plant comprising a plant expressible bar gene and plant expressible genes for the monomeric units of BAY39/40. 1. nucleotide sequence of a control sample (SEQ ID NO:7); 2. nucleotide sequence of a phosphinotricin tolerant line (SEQ ID NO:8); 3-9: nucleotide sequences of phosphinotricin sensitive lines (SEQ ID NO:9-15, respectively).

DESCRIPTION OF DIFFERENT EMBODIMENTS OF THE INVENTION

Figure 1:
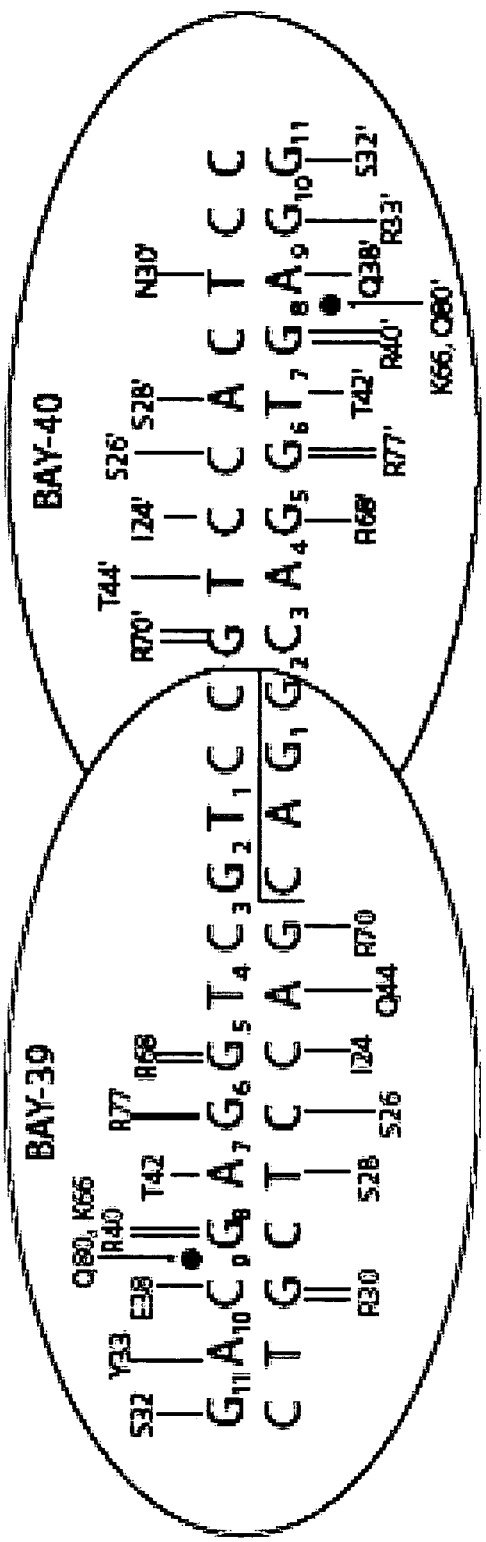
FIG. 1: Schematic representation of the recognition site and interactions with amino acids of the different meganuclease monomeric units BAY 39 and BAY40. The recognition site sequence is set forth in SEQ ID NO:1. The complement of the recognition site sequence is set forth in SEQ ID NO:2.

The current invention is based on the observation that functional re-designed meganucleases can be obtained which specifically recognize and cleave a nucleotide sequence (SEQ ID No. 1 and SEQ ID No. 2—FIG. 1), which can be found in the nucleotide sequence of the coding region of the phosphinotricin acetyltransferase gene from *Streptomyces hygroscopicus* (bar gene) (Thompson, C., Movva, R., Tizard, R., Crameri, R., Davies, J., Lauwereys, M. ans Botterman, J. (1987) Characterization of the herbicide-resistance gene bar from *Streptomyces hygroscopicus. The EMBO Journal* 6: 2519-2523 (Accession X05822), which nucleotide sequence is present in a commonly used selectable marker gene in plant transgenesis.

SEQ ID No. 3 represents the nucleotide sequence of the bar gene. The complement of the recognition site of SEQ ID No. 1 (SEQ ID No. 2) corresponds to the nucleotide sequence of SEQ ID No. 3 from nucleotide 132 to 153. The herein described meganucleases are thus capable of recognizing and cleaving a nucleotide sequence in transgenic plants comprising a plant-expressible gene which has a plant expressible promoter operable linked to a DNA region encoding the phosphinotricin acetyltransferase gene from *Streptomyces hygroscopicus*(bar) and followed by a 3' transcription termination and polyadenylation region functional in plants, the bar coding region comprising the nucleotide sequence which is the complement of the nucleotide sequence of SEQ ID No. 1, such as SEQ ID No. 3.

The bar coding region has been incorporated in a number of transgenic plants which have been, are or will be commercialized including plants comprising the following events:

Chicory (*Cichorium intybus*):
  Events RM3-3, RM3-4, RM3-6 as described in regulatory file 9'7-148-01p
Oilseed rape (*Brassica napus*)
  Event MS1 as described in regulatory files DD95-04 (CA) or 98-278-01p (US)
  Event MS8 as described in regulatory files DD96-17 (CA) or 98-278-01p (US) or WO 2001/041558
  Event RF1 as described in regulatory files DD95-04 (CA) or 98-T78-01p (US)
  Event RF2 as described in regulatory files DD95-04 (CA) or 98-278-01p (US)
  Event RF3 as described in regulatory files DD96-17 (CA) or 98-278-01p (US) or WO 2001/041558
  Events PHY14, PHY35, PHY36 as described in Japanese deregulatory files
Cotton (*Gossypium hirsutum*)
  Event LLcotton 25 as described in regulatory files 02-042-01p (US) or WO 2003/013224
  Event T303-40 as described in WO2008/122406

Event GHB119 as described in regulatory file 08-340-01p (US) or WO2008/151780

Corn (*Zea mays*)

Event TC-6275 (=DAS-06275-8) as described in regulatory file 03-181-01p (US)

Event Bt176 as described in regulatory file 94-319-01p (US)

Event B16 (=DLL25) as described in US deregulation dossier 95-145-01p or WO9506128

Event DBT418 as described in US deregulation dossier 96-291-01p (US)

Event ZMA101

Event CBH351 as described in US deregulation dossier 97-265-01p (US)

Event MS3 as described in US deregulation file 95-228-01p (US)

Event MS6 as described in US deregulation file 98-349-01p (US)

Rice (*Oryza sativa*)

Event LLRice62 as described in US deregulation dossier 98-329-01p or WO 2001/083818

Event LLRICE601 as described in US deregulation dossier 06-234-01p or US patent application 2008289060

Soybean (*Glycine max*)

Events W62 and W98 described in regulatory file 96-068-01p(US)

Transgenic plants containing these events therefore contain a recognition sequence for the meganucleases herein described and are suitable subjects for the methods of the invention. Furthermore, the plant expressible bar gene is used generally as a selectable marker and numerous transgenic plants have been generated which are also suitable subjects for the methods of the invention.

Accordingly, in one embodiment, the invention relates to a method for introducing a foreign DNA molecule at a predefined or preselected site in a (nuclear) genome of a transgenic plant cell comprising the steps of
  a. inducing a double stranded DNA break at the predefined site;
  b. introducing the foreign DNA molecule in said plant cell; and
  c. selecting a plant cell wherein the foreign DNA is introduced at the predefined site;

wherein the predefined site is a nucleotide sequence different from a recognition site for a natural occurring meganuclease and is a nucleotide sequence commonly introduced as part of a transgene in a transgenic plant and wherein double stranded DNA break is induced by introduction of a non-naturally occurring single chain meganuclease or a pair of non-naturally occurring meganuclease monomeric units which recognizes or recognize together the predefined site and induces or induce the double stranded break.

As used herein, "a nucleotide sequence commonly introduced as a part of a transgene in plants" refers to a nucleotide sequence of a DNA region that has been used previously as an element of a chimeric gene introduced in plants, whereby transgenic plants are readily available, particularly whereby the transgenic plants have been, are or will be commercialized and regulatory approvals have been applied for and are publicly available. Several databases are available which summarize and provide information on applications for regulatory approvals including the GM crop database of the Center of Environmental risk assessment which can be consulted online (http://www.cera-gmc.org/?action=gm_crop_database&) or the summary list of the Petitions of Nonregulated Status Granted or Pending by APHIS, available online at http://www.aphis.usda.gov/brs/not_reg.html.

DNA regions commonly introduced as part of a transgene in plants include promoter regions such as the 35S promoter of the CaMV 35S transcript (Odell et al. (1985), *Nature* 313: 810-812); the FMV 35S promoter (Richins R. D., Scholthof H. B., Shepherd R. J. (1987) Sequence of the figwort mosaic virus (caulimovirus group). *Nucleic Acids Research* 15: 8451-8466); the promoter of the small subunit of *Arabidopsis thaliana* Rubisco gene (Krebbers E., Seurinck J., Herdies L., Cashmore A. R., Timko M. P. (1988). Four genes in two diverged subfamilies encode the ribulose-1,5-bisphosphate carboxylase small subunit polypeptides of *Arabidopsis thaliana*. *Plant Molecular Biology*, 11, 745-759); the Casava Vein Mosaic Virus promoter (Verdaguer et al (1996) *Plant Mol. Biol.* 31: 1129 or Verdaguer et al (1998) *Plant Mol. Biol.* 37: 1055); the Acting promoter from *Arabidopsis* (An Y. Q., McDowell J. M., Huang S., McKinney E. C., Chambliss S., Meagher R. B. (1996) Strong, constitutive expression of the *Arabidopsis* ACT2/ACT8 actin subclass in vegetative tissues. *The Plant Journal* 10: 107-121) or rice (McElroy D., Zhang W., Cao J., Wu R. (1990) Isolation of an efficient actin promoter for use in rice transformation. *The Plant Cell* 2: 163-171); the Histone H3 promoter or histone H4 promoter (Chabouté M, Chaubet N, Philipps G, Ehling M and Gigot C (1987) Genomic organization and nucleotide sequences of two histone H3 and two histone H4 genes of *Arabidopsis thaliana*. *Plant Mol. Biol.* 8: 179-191); the promoter of the maize (*Zea mays*) ubiquitin-1 gene (Christensen et al (1992) *Plant Mol. Biol.* 18: 675); 5' UTR leader sequences such as the cab22L leader (Harpster M, Townsend J, Jones J, Bedbrook J and Dunsmuir P. (1988) Relative strengths of the 35S cauliflower mosaic virus, 1', 2' and nopaline synthase promoters in transformed tobacco, sugarbeet and oilseed rape callus tissue. *Mol Gen Genet.* 212:182-190); or 5' tev (Carrington J and Freed D (1990) Cap-independent enhancement of translation by a plant potyvirus 5' nontranslated region. *J Virol* 64(4): 1590-1597); a 3' end of the nopaline synthase gene (Depicker A., Stachel S., Dhaese P., Zambryski P., Goodman H. M. (1982). Nopaline synthase: transcript mapping and DNA sequence. *Journal of Molecular and Applied Genetics* 1, 561-573); a 3' end of the octopine synthase gene (De Greve H., Dhaese P., Seurinck J., Lemmers M., Van Montagu M., Schell J. (1982). Nucleotide sequence and transcript map of the *Agrobacterium tumefaciens* Ti plasmid-encoded octopine synthase gene. *Journal of Molecular and Applied Genetics*, 1, 499-511); the CaMV35S terminator (Sanfaçon et al (1991) *Genes Dev.* 5: 141) transcription termination and polyadenylation region of gene 7 of the octopine type T-DNA vector (D'Haese et al, 1983, *The EMBO Journal*, 2, 419-426) and selectable markers such as bar (Thompson, C., Movva, R., Tizard, R., Crameri, R., Davies, J., Lauwereys, M. ans Botterman, J. (1987) Characterization of the herbicide-resistance gene bar from *Streptomyces hygroscopicus*. *The EMBO Journal* 6: 2519-2523 (Accession X05822)); pat (Wohlleben, W., Arnold, W., Broer, I., Hillemann, D., Strauch, E. and Puhler, A. Nucleotide sequence of the phosphinothricin N-acetyltransferase gene from *Streptomyces viridochromogenes* Tu494 and its expression in *Nicotiana tabacum*. Gene 70 (1), 25-37 (1988)); 2mepsps (sequence 4 from U.S. Pat. No. 6,566,587 or EMBL number AR337832); CP4 (Padgette S. R., Re D., Barry G., Eichholtz D., Delannay X., Fuchs R. L., Kishore G. M., Fraley R. T. (1996). New weed control opportunities: development of soybeans with a Roundup Ready gene. In Herbicide-Resistant Crops: Agricultural, Environmental, Econ . . . , neo Accession V00618; Beck et al (1982) *Gene* 19(3) p 327-336); or hpt (Kaster et al., (1983), NAR 11, 6895-6911).

A preferred DNA region in the context of this invention is the nucleotide sequence of the coding region of the bar gene as mentioned above.

The redesigned meganucleases described herein are based on the naturally occurring meganuclease I-CreI for use as a scaffold. I-CreI is a homing endonuclease found in the chloroplasts of *Chlamydomonas rheinhardti* (Thompson et al. 1992, *Gene* 119, 247-251). This endonuclease is a homodimer that recognizes a pseudo-palindromic 22 bp DNA site in the 23SrRNA gene and creates a double stranded DNA break that is used for the introduction of an intron. I-CreI is a member of a group of endonucleases carrying a single LAGLIDADG motif. LAGLIDADG enzymes contain one or two copies of the consensus motif. Single-motif enzymes, such as I-CreI function as homodimers, whereas double-motif enzymes are monomers with two separate domains. Accordingly, when re-designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease, or may also be achieved by promoting the formation of heterodimers, as described e.g. in WO2007/047859.

The amino acid sequence of a naturally occurring I-CreI monomer is provided as SEQ ID No. 16. To re-design I-CreI monomeric units such that the heterodimers thereof recognize the nucleotide sequence of SEQ ID No. 1 and/or 2 the following amino acids are present at the mentioned positions:

1. in meganuclease unit 1:
   a. S at position 32;
   b. Y at position 33;
   c. E at position 38;
   d. R at position 40;
   e. K at position 66;
   f. Q at position 80;
   g. T at position 42;
   h. R at position 77;
   i. R at position 68;
   j. R at position 70;
   k. Q at position 44;
   l. I at position 24;
   m. S at position 26;
   n. S at position 28;
   o. R at position 30.
2. in meganuclease unit 2:
   p. R at position 70;
   q. T at position 44;
   r. I at position 24;
   s. S at position 26;
   t. S at position 28;
   u. N at position 30;
   v. S at position 32;
   w. R at position 33;
   x. Q at position 38;
   y. Q at position 80;
   z. R at position 40;
   aa. K at position 66;
   bb. T at position 42;
   cc. R at position 77;
   dd. R at position 68.

A schematic representation thereof is provided in FIG. 1.

The re-designed double stranded break inducing enzyme may comprise, but need not comprise, a nuclear localization signal (NLS), such as the NLS of SV40 large T-antigen [Raikhel, *Plant Physiol.* 100: 1627-1632 (1992) and references therein] [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme. It should be noted that if the re-designed meganuclease has been provided with a NLS at the N-terminus of the protein, such as a 10 or 12 amino acid NLS of SV40, the amino acid positions would be shifted (increased) accordingly. Likewise, in the event two monomeric units are linked into a single chain meganuclease, the position of the second unit will also be shifted. The corresponding amino acid positions with regard to the I-CreI amino acid sequence can also be identified by determining the optimal alignment as described below. It will be clear that in the single chain redesigned meganuclease the order of the units is irrelevant, i.e. whether the above unit 1 and 2 occur indeed within that order in the single amino acid chain or unit 2 precedes unit 1 one in the single amino acid chain does not make a difference in order for the two units combined to be able to recognize the target sequence.

Re-designed meganucleases suitable for the invention may comprise an amino acid sequence as represented in SEQ ID No. 5 and 6 (monomeric units which can cleave the recognition site as a heterodimer) or may comprise an amino acid sequence as represented in SEQ ID No. 18 (single chain meganuclease comprising two units represented by amino acid 1 to 167 and from 208 to 362 respectively, linked by a linker sequence represented by amino acids 168 to 205) or may comprise an amino acid sequence comprising the amino acid sequence of SEQ ID No. 18 from 1 to 167 and 206 to 362 (respectively unit 1 and 2 of the single chain meganuclease without the linker).

Conveniently, the redesigned meganuclease(s) can be provided by expression of a plant expressible recombinant gene(s) encoding such meganuclease(s). To this end, a DNA region comprising a nucleotide sequence encoding a re-designed meganuclease or meganuclease monomeric unit can be operably linked to a plant-expressible promoter and a DNA region involved in transcription termination and polyadenylation and introduced into a plant or plant cells. The recombinant gene(s) encoding redesigned meganuclease(s) may be introduced transiently or stably.

For the purpose of the invention, the term "plant-operative promoter" and "plant-expressible promoter" mean a promoter which is capable of driving transcription in a plant, plant tissue, plant organ, plant part, or plant cell. This includes any promoter of plant origin, but also any promoter of non-plant origin which is capable of directing transcription in a plant cell.

Promoters that may be used in this respect are constitutive promoters, such as the promoter of the cauliflower mosaic virus (CaMV) 35S transcript (Hapster et al., 1988, *Mol. Gen. Genet.* 212: 182-190), the CaMV 19S promoter (U.S. Pat. No. 5,352,605; WO 84/02913; Benfey et al., 1989, *EMBO J.* 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, *Plant Mol. Biol.* 29:637-649), T-DNA gene promoters such as the octopine synthase (OCS) and nopaline synthase (NOS) promoters from *Agrobacterium*, and further promoters of genes whose constitutive expression in plants is known to the person skilled in the art.

Further promoters that may be used in this respect are tissue-specific or organ-specific promoters, preferably seed-specific promoters, such as the 2S albumin promoter (Josefsson et al., 1987, *J. Biol. Chem.* 262:12196-12201), the phaseolin promoter (U.S. Pat. No. 5,504,200; Bustos et al., 1989, *Plant Cell* 1. (9):839-53), the legumine promoter (Shirsat et al., 1989, *Mol. Gen. Genet.* 215(2):326-331), the "unknown seed protein" (USP) promoter (Baumlein et al., 1991, *Mol. Gen. Genet.* 225(3):459-67), the napin promoter (U.S. Pat. No. 5,608,152; Stalberg et al., 1996, *Planta* 199:515-519), the *Arabidopsis oleosin* promoter (WO 98/45461), the *Brassica* Bce4 promoter (WO 91/13980), and further promoters of genes whose seed-specific expression in plants is known to the person skilled in the art.

Other promoters that can be used are tissue-specific or organ-specific promoters like organ primordia-specific promoters (An et al., 1996, *Plant Cell* 8: 15-30), stem-specific promoters (Keller et al., 1988, *EMBO J.* 7(12): 3625-3633), leaf-specific promoters (Hudspeth et al., 1989, *Plant Mol. Biol.* 12: 579-589), mesophyl-specific promoters (such as the light-inducible Rubisco promoters), root-specific promoters (Keller et al., 1989, *Genes Dev.* 3: 1639-1646), tuber-specific promoters (Keil et al., 1989, *EMBO J.* 8(5): 1323-1330), vascular tissue-specific promoters (Peleman et al., 1989, *Gene* 84: 359-369), stamen-selective promoters (WO 89/10396, WO 92/13956), dehiscence zone-specific promoters (WO 97/13865), and the like.

Nucleotide sequences encoding re-designed meganucleases suitable for the invention may comprise the nucleotide sequence of SEQ ID No. 4 from nucleotide position 2004 to nucleotide position 2525 or 2522 or the nucleotide sequence of SEQ ID No. 4 from nucleotide position 4885 to nucleotide position 5405 or 5403. To facilitate cloning and other recombinant DNA techniques, it may be advantageous to include an intron functional in plants into the region encoding a meganuclease, particularly a single chain meganuclease. Such an intron may for example comprise the nucleotide sequence of SEQ ID No. 17 from nt position 1606 to 1794.

The DNA region encoding the re-designed meganuclease may be optimized for expression in plants by adapting GC content, codon usage, elimination of unwanted nucleotide sequences. The coding region may further be optimized for expression in plants and the synthetic coding region may have a nucleotide sequence which has been designed to fulfill the following criteria:

a) the nucleotide sequence encodes a functional redesigned homing endonuclease as herein described;
b) the nucleotide sequence has a GC content of about 50% to about 60%;
c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
d) the nucleotide does not comprise a nucleotide sequence selected from the group consisting of CCAAT, ATTGG, GCAAT and ATTGC;
e) the nucleotide sequence does not comprise a sequence selected from the group consisting of ATTTA, AAGGT, AGGTA, GGTA or GCAGG;
f) the nucleotide sequence does not comprise a GC stretch consisting of 7 consecutive nucleotides selected from the group of G or C;
g) the nucleotide sequence does not comprise a AT stretch consisting of 5 consecutive nucleotides selected from the group of A or T; and
h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

An example of such an optimized sequence is represented by SEQ ID No. 17 from nt position 1267 to 1605 and from nt position 1795 to 2541 (wherein the nucleotide sequence encoding the linker present between the two meganuclease units is represented by nt 1957 to 2070).

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another.

However, it will be clear that the DNA molecule of interest may be introduced into the plant cells by any method known in the art, including *Agrobacterium*-mediated transformation but also by direct DNA transfer methods. The transforming DNA molecule can be transferred into plant cells using any conventional method, including but not limited to direct DNA transfer method. As used herein "direct DNA transfer" is any method of DNA introduction into plant cells which does not involve the use of natural *Agrobacterium* spp. and which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, use of silicon whiskers, and bombardment with DNA coated microprojectiles.

The capability of inducing a double stranded break at a preselected site opens up several potential applications. Foreign DNA of interest may be introduced into the preselected site either by homologous recombination, or in the process of non-homologous endjoining. The double stranded break may also be used to induce the formation of small deletions or insertions at the preselected site, thereby potentially inactivating the chimeric gene comprising the nucleotide sequence of the preselected site. The double stranded break at the preselected site will also facilitate replacement of a DNA region in the vicinity of that site for a DNA region of interest e.g. as described in WO 06/105946, WO08/037,436 or WO08/148,559.

To insert foreign DNA by homologous recombination at the preselected site, the foreign DNA may be comprised within a repair DNA, wherein the foreign DNA is flanked by at least one flanking DNA region having a nucleotide sequence which is similar to the nucleotide sequence of the DNA region upstream or downstream of the preselected site. The repair DNA may comprise the foreign DNA to be inserted flanked by two flanking DNA regions, upstream and downstream of the foreign DNA and which are similar to nucleotide sequence of the DNA region upstream or downstream of the preselected sites. Alternatively, the foreign DNA may be integrated as such, i.e. without flanking sequences with homology to the region around the predefined target site (without any further DNA), for integration by non-homologous end-joining As used herein "a flanking DNA region" is a DNA with a nucleotide sequences having homology to the DNA regions respectively upstream or downstream of the target DNA sequence or preselected site. This allows to better control the insertion of the foreign DNA or the DNA molecule of interest. Indeed, integration by homologous recombination will allow precise joining of the foreign DNA fragment to the plant nuclear genome up to the nucleotide level.

The flanking DNA regions may vary in length, and should be at least about 10 nucleotides in length. However, the flanking region may be as long as is practically possible (e.g. up to about 100-150 kb such as complete bacterial artificial chromosomes (BACs)).

Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA. Furthermore, to achieve exchange of the target DNA sequence without changing the DNA sequence of the adjacent DNA sequences, the flanking DNA sequences should preferably be identical to the DNA regions flanking the preselected site.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest. Thus, by choosing the appropriate configuration of the foreign DNA for repair of the double stranded DNA break, by introducing a foreign DNA molecule according to the methods of the invention, in addition to insertions, one can also make targeted replacements or targeted deletions of the genomic region located between the homology regions.

The foreign DNA to be inserted may also comprise a selectable or screenable marker, which may or may not be removed after insertion.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes.

The selection of the plant cell or plant wherein the selectable or screenable marker and the rest of the foreign DNA molecule has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the origination of the transformed plant cells is by random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

It will be clear that the methods according to the invention allow insertion of any DNA of interest including DNA comprising a nucleotide sequence with a particular nucleotide sequence signature e.g. for subsequent identification. The DNA of interest may also be one or more plant expressible gene(s) including but not limited to a herbicide tolerance gene, an insect resistance gene, a disease resistance gene, an abiotic stress resistance gene, an enzyme involved in oil biosynthesis or carbohydrate biosynthesis, an enzyme involved in fiber strength and/or length, an enzyme involved in the biosynthesis of secondary metabolites.

Herbicide-tolerance genes include a gene encoding the enzyme 5-enolpyruvylshikimate-3-phosphate synthase (EPSPS). Examples of such EPSPS genes are the AroA gene (mutant CT7) of the bacterium Salmonella typhimurium (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995.

Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide tolereance genes may encode an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Herbicide-tolerance genes may also confer tolerance to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide tolerance genes encode variant ALS enzymes (also known as acetohydroxyacid synthase, AHAS) as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerance genes are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerance genes are described in for example WO 07/024,782 and U.S. Patent Application No. 61/288,958.

Insect resistance gene may comprise a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5);

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

An "insect-resistant gene as used herein, further includes transgenes comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Abiotic Stress Tolerance Genes Include 1) a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) a transgene capable of reducing the expression and/or the activity of the PARG encoding genes of the plants or plants cells, as described e.g. in WO 2004/090140.

3) a transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

The invention also provides a method for introducing a deletion at a predefined or preselected site in a (nuclear) genome of a transgenic plant cell comprising the steps of
  a. inducing a double stranded DNA break at the predefined site; and
  b. selecting a plant cell having a deletion at said predefined site;
wherein the predefined site is a nucleotide sequence different from a recognition site for a natural occurring meganuclease and is a nucleotide sequence commonly introduced as part of a transgene in a transgenic plant and wherein double stranded DNA break is induced by introduction of a non-naturally occurring single chain meganuclease or a pair of non-naturally occurring meganuclease monomeric units which recognizes or recognize together the predefined site and induces or induce the double stranded break.

It is also an embodiment of the invention to provide chimeric genes encoding re-designed meganucleases as herein described, wherein the chimeric gene comprise a plant expressible promoter operably linked to a DNA region encoding a protein comprising an amino acid sequence corresponding to the amino acid sequence of I-CreI as a scaffold comprising a S at position 32; Y at position 33; E at position 38; R at position 40; K at position 66; Q at position 80; T at position 42; R at position 77; R at position 68; R at position 70; Q at position 44; I at position 24; S at position 26; S at position 28 and R at position 30 or R at position 70; T at position 44; I at position 24; S at position 26; S at position 28; N at position 30; S at position 32; R at position 33; Q at position 38; Q at position 80; R at position 40; K at position 66; T at position 42; R at position 77 and R at position 68 (positions with respect to the amino acid sequence of I-CreI, corresponding amino acid positions in redesigned meganucleases can be determined by alignment), such as a protein comprising the amino acid sequence of SEQ ID 5 or SEQ ID 6 or a protein comprising the amino acid sequence of SEQ ID No. 18, or a protein comprising the amino acid sequence of SEQ ID NO 18 from position 1 to 167 and the amino acid sequence of SEQ ID NO 18 from position 206 to 362.

It will be appreciated that the means and methods of the invention may be used in any plant including corn, tobacco, cereal plants including wheat, oat, barley, rye, rice, turfgrass, sorghum, millet or sugarcane plants. The methods of the invention can also be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet and sugar beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants generated according to the methods of the invention. Gametes, seeds, embryos, either zygotic or somatic, progeny or hybrids of plants comprising the DNA insertion events, which are produced by traditional breeding methods, are also included within the scope of the present invention. Such plants may contain a heterologous or foreign DNA sequence inserted at or instead of a target sequence, and will only be different from their progenitor plants by the presence of this heterologous DNA or DNA sequence post exchange.

The plants obtained by the methods described herein may be further crossed by traditional breeding techniques with other plants to obtain progeny plants comprising the targeted DNA insertion events obtained according to the present invention.

The plants and seeds according to the invention may be further treated with a chemical compound, such as a chemical compound selected from the following lists:
  Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam
  Fruits/Vegetables Insecticides: Aldicarb, *Bacillus thuriengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid
  Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin Cereals herbicides: 2.4-D, amidosulfuron, bromoxynil, carfentrazone-e, chlorotoluron, chlorsulfuron, clodinafop-p, clopyralid, dicamba, diclofop-m, diflufenican, fenoxaprop, florasulam, flucarbazone-na, flufenacet, flupyrsulfuron-m, fluroxypyr, flurtamone, glyphosate, iodosulfuron, ioxynil, isoproturon, mcpa, mesosulfuron, metsulfuron, pendimethalin, pinoxaden, propoxycarbazone, prosulfocarb, pyroxsulam, sulfosulfuron, thifensulfuron, tralkoxydim, triasulfuron, tribenuron, trifluralin, tritosulfuron Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor Maize Herbicides: Atrazine, Alachlor, Bromoxynil, Acetochlor, Dicamba, Clopyralid, (S-)Dimethenamid, Glufosinate, Glyphosate, Isoxaflutole, (S-) Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Tebupirimphos, Ethiprole, Cyazypyr, Thiacloprid, Acetamiprid, Dinetofuran, Avermectin Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chiorpyriphos, Etofenprox, Carbofuran, Benfuracarb, Sulfoxaflor Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat
Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2 (5H)-on As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc. As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The following non-limiting Examples describe the use of a re-designed meganuclease to modify plants at the site of a bar coding region already present in the plant genome.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications and publications mentioned herein are hereby incorporated by reference, in their entireties, for all purposes.

Throughout the description and Examples, reference is made to the following sequences:

SEQ ID No. 1: nucleotide sequence of the recognition site of the re-designed meganucleases BAY 39/BAY40

SEQ ID No. 2: nucleotide sequence of the complement of the recognition site of the re-designed meganucleases BAY 39/BAY40

SEQ ID No. 3: nucleotide sequence of the bar gene coding region

SEQ ID No. 4: nucleotide sequence of the vector pCV177 expressing a pair of heterodimer meganucleases BAY 39 and BAY40

SEQ ID No. 5: amino acid sequence of the meganuclease BAY39/40 monomeric unit 2 ("40")

SEQ ID No. 6: amino acid sequence of the meganuclease BAY39/40 monomeric unit 1 ("39")

SEQ ID No. 7: nucleotide sequence of the PCR amplicon of the bar coding region around the BAY39/40 recognition site (control)

SEQ ID No. 8: nucleotide sequence of the PCR amplicon of the bar coding region around the BAY39/40 recognition site (PPT tolerant line)

SEQ ID No. 9: nucleotide sequence of the PCR amplicon of the bar coding region around the BAY39/40 recognition site (PPT sensitive line 1)

SEQ ID No. 10: nucleotide sequence of the PCR amplicon of the bar coding region around the BAY39/40 recognition site (PPT sensitive line 2)

SEQ ID No. 11: nucleotide sequence of the PCR amplicon of the bar coding region around the BAY39/40 recognition site (PPT sensitive line 3)

SEQ ID No. 12: nucleotide sequence of the PCR amplicon of the bar coding region around the BAY39/40 recognition site (PPT sensitive line 4)

SEQ ID No. 13: nucleotide sequence of the PCR amplicon of the bar coding region around the BAY39/40 recognition site (PPT sensitive line 5)

SEQ ID No. 14: nucleotide sequence of the PCR amplicon of the bar coding region around the BAY39/40 recognition site (PPT sensitive line 6)

SEQ ID No. 15: nucleotide sequence of the PCR amplicon of the bar coding region around the BAY39/40 recognition site (PPT sensitive line 7)

SEQ ID No. 16: amino acid sequence of I-CreI natural variant (monomer)

SEQ ID No. 17: nucleotide sequence of the vector pCV170 expressing a single chain BAY39/BAY40 meganuclease SEQ ID No. 18: amino acid sequence of the single chain BAY39/40 meganuclease

EXAMPLES

All re-designed meganucleases described herein have been designed by Precision BioSciences Inc., 104 T.W. Alexander Drive, Research Triangle Park, N.C. 27713.

Example 1

Description of the T-DNA Vectors Encoding Re-Designed Meganucleases According to the Invention Using conventional recombinant DNA techniques a chimeric gene encoding a pair of re-designed meganuclease monomers which as a heterodimer recognize the nucleotide sequence of SEQ ID No. 1 or 2 (hd BAY39/40) was constructed, comprising the following operably linked DNA fragments:
- a DNA region encoding the CaMV35S promoter (SEQ ID No 6 from nt position 1516 to nt position 1933, such as SEQ ID No 4 from nt position 1516 to nt position 1997)
- a DNA region comprising the BAY 39/40 monomeric unit 2 encoding region, operably linked to a SV40 NLS at the N-terminus (SEQ ID No 4 from nt position 2004 to 2525 including the stop codon, or to 2522 excluding the stopcodon)
- a DNA region involved in 3' end transcription termination and polyadenylation from nopaline synthase gene (SEQ ID No 4 from nt position 2530 to 2783)
- a DNA region encoding the CaMV35S promoter (SEQ ID No 4 from nt position 4397 to nt position 4814, such as SEQ ID No 4 from nt position 4397 to nt position 4878)
- a DNA region comprising the BAY 39/40 monomeric unit 1, operably linked to a SV40 NLS at the N-terminus (SEQ ID No 4 from nt position 4885 to 5405, including the stopcodon, or to 5403, excluding the stop codon)
- a DNA region involved in 3' end transcription termination and polyadenylation from nopaline synthase gene (SEQ ID No 4 from nt position 5411 to 5664).

The nucleotide sequence of the resulting plasmid is represented in SEQ ID No. 4.

Using conventional recombinant DNA techniques a chimeric gene encoding a single chain re-designed meganuclease which recognize the nucleotide sequence of SEQ ID No. 1 or 2 (sc BAY39/40) was constructed, comprising the following operably linked DNA fragments:
- a DNA region encoding the CaMV35S promoter (SEQ ID No 17 from nt position 691 to nt position 1223)
- leader sequence from *Arabidopsis thaliana* rbcS ATS1A gene; SEQ ID No 17 from nt position 1224 to nt position 1266; Krebbers et al. 1988 Plant Molecular Biology 11:745-759)
- a DNA region encoding the N-terminal region of the single chain BAY 39/40 meganuclease, operably linked to a SV40 NLS at the N-terminus, optimized for expression in tobacco (SEQ ID No 17 from nt position 1267 to 1605)
- a DNA region encoding the second intron of the potato light inducible tissue-specific ST-LS1 gene (SEQ ID No 17 from nt position 1606 to 1794; X04753; Eckes et al. 1986 Mol. Gen. Genet. 205, 14-22)
- a DNA region encoding the C-terminal region of the single chain BAY 39/40 meganuclease (SEQ ID No 17 from nt position 1795 to 1798, including the stop codon, or to 2541, excluding the stop codon), including DNA region encoding a linker sequence (SEQ ID No 17 from nt position 1757 to 2070), optimized for expression in tobacco.
- a DNA region involved in 3' end transcription termination and polyadenylation from 35S gene (SEQ ID No. 17 from nt position 2545 to 2678).

The nucleotide sequence of the resulting plasmid is represented in SEQ ID No. 17.

Example 2

Description of the Target Tobacco Line and Assay

In order to develop an assay for double stranded DNA break induction, a phosphinotricin (PPT) tolerant tobacco transgenic plant line was selected that contained a bar coding region under control of a plant-expressible promoter.

This transgenic line was used as starting material in a transformation wherein the chimeric genes encoding hd BAY39/40 meganucleases were either stably or transiently introduced together with a plant expressible chimeric gene comprising a hygromycinphosphotransferase conferring resistance to hygromycine.

After double stranded DNA break induction at the recognition site in the bar coding region through expression of the plant expressible chimeric genes encoding the BAY39/40 heterodimer, the break can be repaired by non-homologous end-joining in the absence of repair DNA, resulting in deletion or insertion of one or more base pairs, thereby disrupting the bar coding region, resulting in phosphinotricin sensitivity.

Several plant lines exhibiting phosphinotricine sensitivity and hygromycin resistance were selected. From these plant lines a DNA fragment was amplified by PCR using primers located at either side of the recognition site (SEQ ID No 1 or 2) in the bar coding region, and the nucleotide sequence of the amplicons was determined. An alignment of the different nucleotide sequences is represented in FIG. 5.

It is clear that in the PPT sensitive plant lines (3 to 9), the recognition site for BAY39/40 has been altered by deletion (3 to 8) or insertion (9) whereas no alteration was found in PPT resistant plant lines (2).

From these experiments it can thus be concluded that hdBAY39/40 exhibits cleavage activity at the preselected site.

Example 3

Targeted Insertion by Non-Homologous End-Joining

Co-delivery of pCV177 comprising the chimeric genes encoding hd BAY39/40 meganucleases or pCV170 comprising the chimeric gene encoding the sc BAY39/40 with repair DNA comprising a selectable marker such as a plant-expressible chimeric gene comprising a 2mepsp coding region (without further homology to the target region) to plant cells comprising a plant expressible chimeric bar gene integrated in their genome and selection of phosphinotricin sensitive plants tolerant to the selection compound such as glyphosate allows the identification of the plant cells wherein repair DNA sequences are integrated in the bar coding region.

Example 4

Targeted Insertion by Homologous End-Joining

Co-delivery of either pCV177, comprising the chimeric genes encoding hd BAY39/40 meganucleases or pCV170, comprising the chimeric gene encoding the sc BAY39/40, with repair DNA comprising a selectable marker such as a plant-expressible chimeric gene comprising a 2mepsp coding region flanked upstream by flanking sequences comprising a nucleotide sequence with sequence similarity to the bar coding region of SEQ ID No 3 from nucleotide 1 to nucleotide 132 and flanked downstream by flanking sequences comprising a nucleotide sequence with sequence similarity to the bar coding region of SEQ ID No 3 from nucleotide 154 to nucleotide 552, into plant cells comprising a plant expressible chimeric bar gene integrated in their genome and selection of phosphinotricin sensitive plants tolerant to the selection compound such as glyphosate allows the identification of the plant cells wherein the repair DNA is integrated in the bar coding region.

Example 5

Targeted Double Stranded DNA Break Induction Using BAY39/40 Single Chain and Heterodimeric Meganuclease in Cotton Embryogenic calli from PPT-resistant cotton plants containing a chimeric gene comprising the bar gene under control of the CSVMV promoter were grown on M100 substrate (MS salts, B5 vitamins, MES 0.5 g/L, $MgCl_2.6H_2O$ 0.94 g/L, gelrite 2 g/L, glucose 30 g/L, pH 5.8) with 2 g/L active carbon. These calli were subjected to microparticle bombardment, using a BioRAD PPS_1000/He Biolistic Particle delivering system essentially as described by Sanford et al., 1992 whereby the particles were coated with either the pCV 177 vector encoding the heterodimeric BAY39/40 meganuclease or the pCV170 vector encoding the single chain BAY39/40 meganuclease. A co-delivery was done of the meganuclease vector with a vector containing the 2mEPSPS gene under control of a plant-expressible promoter conferring glyphosate tolerance as a selectable marker gene. After bombardment, the calli were transferred to a medium containing 1 mM glyphosate, resulting in about 3000 glyphosate resistant embryogenic calli. Of these, 85 events appeared PPT sensitive, of which 79 events were further molecularly analyzed. These 79 events were characterized for genotype by PCR using primers flanking the target site and subsequent sequencing of the PCR product. The absence of a PCR product is indicative of a large deletion around the target site (table 1).

TABLE 1

Characterization of PPT-sensitive glyphosate-resistant transformation events.

| PCR product obtainable | # events | change at target site | # events |
|---|---|---|---|
| pCV170 (sc) | | | |
| no | 11 | large deletion | 11 |
| yes | 8 | no mutation | 6 |
| | | replacement/insertion | 1 |
| | | deletion | 1 |
| pCV177 (hd) | | | |
| no | 33 | large deletion | 33 |
| yes | 27 | no mutation | 19 |
| | | insertion | 4 |
| | | deletion | 4 |

Thus, these results demonstrate that both the single chain as well as the heterodimeric BAY39/40 meganuclease are capable of inducing a targeted double stranded DNA break at the desired position and that targeted deletion, replacement and insertion events can be obtained using these meganucleases in cotton.

The invention claimed is:

1. A method for introducing a foreign DNA molecule at a predefined site in a genome of a plant cell comprising the steps of
   a. inducing a double stranded DNA break at said predefined site;
   b. introducing said foreign DNA molecule in said plant cell; and
   c. selecting a plant cell wherein said foreign DNA is introduced at said predefined site; characterized in that said predefined site is comprised within SEQ ID No. 3 and that said double stranded DNA break is induced by introduction of a single chain meganuclease or a pair of meganucleases which recognizes or recognize in concert said predefined site and induces or induce said double stranded break.

2. A method for introducing a foreign DNA molecule at a predefined site in a genome of a plant cell comprising the steps of
   a. inducing a double stranded DNA break at said predefined site;
   b. introducing said foreign DNA molecule in said plant cell; and
   c. selecting a plant cell wherein said foreign DNA is introduced at said predefined site;
   characterized in that said predefined site comprises the nucleotide sequence of SEQ ID No. 1 or SEQ ID No. 2 and that said double stranded DNA break is induced by introduction of a single chain meganuclease or a pair of meganucleases which recognizes or recognize in concert said predefined site and induces or induce said double stranded break.

3. The method according to any one of claim 1 or 2, wherein said meganuclease or said pair of meganucleases is/are derived from I-CreI and wherein the following amino acids are present in meganuclease unit 1:
   a. S at position 32;
   b. Y at position 33;
   c. E at position 38;
   d. R at position 40;
   e. K at position 66;
   f. Q at position 80;
   g. T at position 42;
   h. R at position 77;
   i. R at position 68;
   j. R at position 70;
   k. Q at position 44;
   l. I at position 24;
   m. S at position 26;
   n. S at position 28;
   o. R at position 30;

and wherein the following amino acids are present in meganuclease unit 2:
   p. R at position 70;
   q. T at position 44;
   r. I at position 24;
   s. S at position 26;
   t. S at position 28;
   u. N at position 30;
   v. S at position 32;
   w. R at position 33;
   x. Q at position 38;
   y. Q at position 80;
   z. R at position 40;
   aa. K at position 66;
   bb. T at position 42;
   cc. R at position 77;
   dd. R at position 68.

4. The method according to any one of claim 1 or 2, wherein said pair of meganucleases obligatory forms heterodimers or wherein said meganuclease is a single chain meganuclease comprising two domains derived from I-CreI covalently connected by a linker.

5. The method according to any one of claim 1 or 2, wherein said pair of meganucleases comprises the amino acid sequence of SEQ ID No. 5 and SEQ ID No. 6, respectively, or wherein said pair of meganucleases is encoded by a nucleic acid comprising the nucleotide sequence of SEQ ID No. 4 from nucleotide position 2004 to nucleotide position 2525 or to 2522 and the nucleotide sequence of SEQ ID No. 4 from nucleotide position 4885 to nucleotide position 5405 or to 5403 or wherein said single chain meganuclease comprises the amino acid sequence of SEQ ID No. 18 from position 1 to 167 and from position 206 to 362 or wherein said single chain meganuclease is encoded by a nucleic acid molecule comprising the nucleotide sequence of SEQ ID No. 17 from nucleotide position 1267 to 1605 and from 1796 to 1956 and from 2071 to 2544 or 2541, or said single chain meganuclease is encoded by a nucleic acid molecule comprising the nucleotide sequence of SEQ ID No. 17 from nucleotide position 1267 to 1605 and from 1796 to 2544 or 2541.

6. The method according to any one of claim 1 or 2, wherein said foreign DNA is comprised within a repair DNA, said repair DNA comprising at least one flanking nucleotide sequence homologous to the upstream or downstream sequence of the nucleotide sequence of SEQ ID No. 1.

7. The method according to any one of claim 1 or 2, wherein said meganuclease or said pair of meganucleases is expressed from a chimeric gene or a pair of chimeric genes, each comprising a plant expressible promoter operably linked to a coding region encoding said meganuclease or one of said pair of meganucleases, and further operationally linked to a DNA region involved in transcription termination and polyadenylation functional in a plant cell.

8. The method according to any one of claim 1 or 2, wherein said foreign DNA comprises a selectable marker gene.

9. The method according to any one of claim 1 or 2, wherein said foreign DNA comprises a plant expressible gene of interest, said gene of interest optionally being selected from a herbicide tolerance gene, an insect resistance gene, a disease resistance gene, an abiotic stress resistance gene, an enzyme involved in oil biosynthesis, carbohydrate biosynthesis, an enzyme involved in fiber strength or fiber length, an enzyme involved in biosynthesis of secondary metabolites.

10. The method according to any one of claim 1 or 2 wherein said plant cell is further regenerated into a plant.

\* \* \* \* \*

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial
<220> FEATURE:
<223> OTHER INFORMATION: Recognition site for BAY39/40

<400> SEQUENCE: 1
gacgaggtcg tccgtccact cc                                              22

<210> SEQ ID NO 2
<211> LENGTH: 22
<212> TYPE: DNA
<213> ORGANISM: Artificial
<220> FEATURE:
<223> OTHER INFORMATION: Complement of the recognition site for BAY39/40

<400> SEQUENCE: 2
ggagtggacg gacgacctcg tc                                              22
```

<210> SEQ ID NO 3
<211> LENGTH: 552
<212> TYPE: DNA
<213> ORGANISM: Artificial
<220> FEATURE:
<223> OTHER INFORMATION: Coding region of the phosphinotricin
      actelyltransferase gene derived from S. hygroscopicus (bar)

<400> SEQUENCE: 3

| | | | | | |
|---|---|---|---|---|---|
| atgagcccag | aacgacgccc | ggccgacatc | cgccgtgcca | ccgaggcgga | catgccggcg | 60 |
| gtctgcacca | tcgtcaacca | ctacatcgag | acaagcacgg | tcaacttccg | taccgagccg | 120 |
| caggaaccgc | aggagtggac | ggacgacctc | gtccgtctgc | gggagcgcta | tccctggctc | 180 |
| gtcgccgagg | tggacggcga | ggtcgccggc | atcgcctacg | cgggcccctg | gaaggcacgc | 240 |
| aacgcctacg | actggacggc | cgagtcgacc | gtgtacgtct | ccccccgcca | ccagcggacg | 300 |
| ggactgggct | ccacgctcta | cacccacctg | ctgaagtccc | tggaggcaca | gggcttcaag | 360 |
| agcgtggtcg | ctgtcatcgg | gctgcccaac | gacccgagcg | tgcgcatgca | cgaggcgctc | 420 |
| ggatatgccc | ccgcggcat | gctgcgggcg | ccggcttca | agcacgggaa | ctggcatgac | 480 |
| gtgggtttct | ggcagctgga | cttcagcctg | ccggtaccgc | ccgtccggt | cctgcccgtc | 540 |
| accgagatct | ga | | | | | 552 |

<210> SEQ ID NO 4
<211> LENGTH: 6234
<212> TYPE: DNA
<213> ORGANISM: Artificial
<220> FEATURE:
<223> OTHER INFORMATION: Plasmid pCV177
<220> FEATURE:
<221> NAME/KEY: CDS
<222> LOCATION: (2004)..(2522)
<220> FEATURE:
<221> NAME/KEY: CDS
<222> LOCATION: (4885)..(5403)

<400> SEQUENCE: 4

| | | | | | |
|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aacccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attcccttt | 240 |
| ttgcggcatt | ttgccttcct | gttttgctc | acccagaaac | gctggtgaaa | gtaaaagatg | 300 |
| ctgaagatca | gttgggtgca | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |

```
cccgtatcgt agttatctac acgacgggga gtcaggcaac tatggatgaa cgaaatagac      1020
agatcgctga gataggtgcc tcactgatta agcattggta actgtcagac caagtttact      1080
catatatact ttagattgat ttaaaacttc atttttaatt taaaaggatc taggtgaaga      1140 tccttttttgc tagcgagagg cggtttgcgt attggctaga gcagcttgcc aacatggtgg     1200
agcacgacac tctcgtctac tccaagaata tcaaagatac agtctcagaa gaccaaaggg      1260
ctattgagac ttttcaacaa agggtaatat cgggaaacct cctcggattc cattgcccag      1320
ctatctgtca cttcatcaaa aggacagtag aaaggaagg tggcacctac aaatgccatc       1380
attgcgataa aggaaaggct atcgttcaag atgcctctgc cgacagtggt cccaaagatg      1440 gaccccacc cacgaggagc atcgtggaaa agaagacgt tccaaccacg tcttcaaagc        1500
aagtggattg atgtgaacat ggtggagcac gacactctcg tctactccaa gaatatcaaa      1560
gatacagtct cagaagacca aagggctatt gagactttc aacaagggt aatatcggga        1620 aacctcctcg gattccattg cccagctatc tgtcacttca tcaaaaggac agtagaaaag      1680
gaaggtggca cctacaaatg ccatcattgc gataaaggaa aggctatcgt tcaagatgcc      1740
tctgccgaca gtggtcccaa agatggaccc caccacga ggagcatcgt ggaaaaagaa        1800
gacgttccaa ccacgtcttc aaagcaagtg gattgatgtg atatctccac tgacgtaagg     1860
gatgacgcac aatcccacta tccttcgcaa gacccttcct ctatataagg aagttcattt     1920
catttggaga ggacacgctg aaatcaccag tctctctcta caaatctatc tctctcgagc     1980
tttcgcagat ctgtcgaacc acc atg gca ccg aag aag aag cgc aag gtg cat     2033
                            Met Ala Pro Lys Lys Lys Arg Lys Val His
                             1               5                  10 atg aac acc aag tac aac aag aag ttc ctg ctc tac ctg gcg ggc ttc       2081
Met Asn Thr Lys Tyr Asn Lys Lys Phe Leu Leu Tyr Leu Ala Gly Phe
             15                  20                  25 gtg gac ggg gac ggc tcc atc atc gcc tcc atc tcc ccg aac cag tcc       2129
Val Asp Gly Asp Gly Ser Ile Ile Ala Ser Ile Ser Pro Asn Gln Ser
         30                  35                  40 cgc aag ttc aag cat cag ctg cgc ctc acc ttc acc gtc acc cag aag       2177
Arg Lys Phe Lys His Gln Leu Arg Leu Thr Phe Thr Val Thr Gln Lys
     45                  50                  55 aca cag cgc cgt tgg ttc ctc gac aag ctg gtg gac aag atc ggg gtg       2225
Thr Gln Arg Arg Trp Phe Leu Asp Lys Leu Val Asp Lys Ile Gly Val
 60                  65                  70 ggc aag gtg cgc gac cgc ggc agc gtc tcc gac tac cgc ctg tcc cag       2273
Gly Lys Val Arg Asp Arg Gly Ser Val Ser Asp Tyr Arg Leu Ser Gln
75                  80                  85                  90 atc aag cct ctg cac aac ttc ctg acc cag ctc cag ccc ttc ctg aag       2321
Ile Lys Pro Leu His Asn Phe Leu Thr Gln Leu Gln Pro Phe Leu Lys
                 95                 100                 105 ctc aag cag aag cag gcc aac ctc gtg ctg aag atc atc gag cag ctg       2369
Leu Lys Gln Lys Gln Ala Asn Leu Val Leu Lys Ile Ile Glu Gln Leu
             110                 115                 120 ccc tcc gcc aag gaa tcc ccg gac aag ttc ctg gag gtg tgc acc tgg       2417
Pro Ser Ala Lys Glu Ser Pro Asp Lys Phe Leu Glu Val Cys Thr Trp
         125                 130                 135 gtg gac cag atc gcc gct ctg aac gac tcc aag acc cgc aag acc act       2465
Val Asp Gln Ile Ala Ala Leu Asn Asp Ser Lys Thr Arg Lys Thr Thr
     140                 145                 150 tcc gag acc gtc cgc gcc gtt cta gac agt ctc tcc gag aag aag aag       2513
Ser Glu Thr Val Arg Ala Val Leu Asp Ser Leu Ser Glu Lys Lys Lys
155                 160                 165                 170 tcg tcc ccc tagcatgccg ttcaaacatt tggcaataaa gtttcttaag               2562
Ser Ser Pro
```

Ser Ser Pro

```
attgaatcct gttgccggtc ttgcgatgat tatcatataa tttctgttga attacgttaa   2622
gcatgtaata attaacatgt aatgcatgac gttatttatg agatgggttt ttatgattag   2682
agtcccgcaa ttatacattt aatacgcgat agaaaacaaa atatagcgcg caaactagga   2742
taaattatcg cgcgcggtgt catctatgtt actagatcgg gcccgggaat aaaatatctt   2802
tattttcatt acatctgtgt gttggttttt tgtgtgaatc gatagtacta acatacgctc   2862
tccatcaaaa caaaacgaaa caaaacaaac tagcaaaata ggctgtcccc agtgcaagtg   2922
caggtgccag aacatttctc tgctagcctc atgaccaaaa tcccttaacg tgagttttcg   2982
ttccactgag cgtcagaccc cgtagaaaag atcaaaggat cttcttgaga tccttttttt   3042
ctgcgcgtaa tctgctgctt gcaaacaaaa aaccaccgc taccagcggt ggtttgtttg    3102
ccggatcaag agctaccaac tcttttccg aaggtaactg gcttcagcag agcgcagata    3162
ccaaatactg ttcttctagt gtagccgtag ttaggccacc acttcaagaa ctctgtagca   3222
ccgcctacat acctcgctct gctaatcctg ttaccagtgg ctgctgccag tggcgataag   3282
tcgtgtctta ccgggttgga ctcaagacga tagttaccgg ataaggcgca gcggtcgggc   3342
tgaacggggg gttcgtgcac acagcccagc ttggagcgaa cgacctacac cgaactgaga   3402
tacctacagc gtgagctatg agaaagcgcc acgcttcccg aagggagaaa ggcggacagg   3462
tatccggtaa cgcgcagggt cggaacagga gagcgcacga gggagcttcc agggggaaac   3522
gcctggtatc tttatagtcc tgtcgggttt cgccacctct gacttgagcg tcgatttttg   3582
tgatgctcgt cagggggggcg agcctatgg aaaaacgcca gcaacgcggc ctttttacgg   3642
ttcctggcct tttgctggcc ttttgctcac atgttctttc ctgcgttatc ccctgattct   3702
gtggataacc gtattaccgc ctttgagtga gctgataccg ctcgccgcag ccgaacgacc   3762
gagcgcagcg agtcagtgag cgaggaagcg gaagagcgcc caatacgcaa accgcctctc   3822
cccgcgcgtt ggccgattca ttaatgcagc tggcacgaca ggtttcccga ctggaaagcg   3882
ggcagtgagc gcaacgcaat taatgtgagt tagctcactc attaggcacc ccaggcttta   3942
cactttatgc ttccggctcg tatgttgtgt ggaattgtga gcggataaca atttcacaca   4002
ggaaacagct atgaccatga ttacgccaag cttgagaggc ggtttgcgta ttggctagag   4062
cagcttgcca acatggtgga gcacgacact ctcgtctact ccaagaatat caaagataca   4122
gtctcagaag accaaagggc tattgagact tttcaacaaa gggtaatatc gggaaacctc   4182
ctcggattcc attgcccagc tatctgtcac ttcatcaaaa ggacagtaga aaaggaaggt   4242
ggcacctaca aatgccatca ttgcgataaa ggaaaggcta tcgttcaaga tgcctctgcc   4302
gacagtggtc ccaaagatgg acccccaccc acgaggagca tcgtggaaaa agaagacgtt   4362
ccaaccacgt cttcaaagca agtggattga tgtgaacatg gtggagcacg acactctcgt   4422
ctactccaag aatatcaaag atacagtctc agaagaccaa agggctattg agacttttca   4482
acaagggta atatcgggaa acctcctcgg attccattgc ccagctatct gtcacttcat   4542
caaaaggaca gtagaaaagg aaggtggcac ctacaaatgc catcattgcg ataaaggaaa   4602
ggctatcgtt caagatgcct ctgccgacag tggtcccaaa gatggacccc cacccacgag   4662
gagcatcgtg gaaaagaag acgttccaac cacgtcttca aagcaagtgg attgatgtga   4722
tatctccact gacgtaaggg atgacgcaca atcccactat ccttcgcaag acccttcctc   4782
tatataagga agttcatttc atttggagag gacacgctga atcaccagt ctctctctac    4842
aaatctatct ctctcgagct ttcgcagatc tgtcgaacca cc atg gca ccg aag      4896
```

```
                        Met Ala Pro Lys
                                175 aag aag cgc aag gtg cat atg aac acc aag tac aac gag gag ttc ctg    4944
Lys Lys Arg Lys Val His Met Asn Thr Lys Tyr Asn Glu Glu Phe Leu
        180                 185                 190 ctc tac ctg gcg ggc ttc gtg gac ggg gac ggc tcc atc atc gcc tcc    4992
Leu Tyr Leu Ala Gly Phe Val Asp Gly Asp Gly Ser Ile Ile Ala Ser
195                 200                 205 atc tcc ccg cgc cag tcc tac aag ttc aag cat gag ctg cgc ctc acc    5040
Ile Ser Pro Arg Gln Ser Tyr Lys Phe Lys His Glu Leu Arg Leu Thr
210                 215                 220                 225 ttc cag gtc acg cag aag aca cag cgc gtt tgg ttc ctc gac gag ctg    5088
Phe Gln Val Thr Gln Lys Thr Gln Arg Arg Trp Phe Leu Asp Glu Leu
            230                 235                 240 gtg gac gag atc ggg gtg ggc aag gtg cgc gac cgc ggc agc gtc tcc    5136
Val Asp Glu Ile Gly Val Gly Lys Val Arg Asp Arg Gly Ser Val Ser
        245                 250                 255 gac tac cgc ctg tcc cag atc aag cct ctg cac aac ttc ctg acc cag    5184
Asp Tyr Arg Leu Ser Gln Ile Lys Pro Leu His Asn Phe Leu Thr Gln
260                 265                 270 ctc cag ccc ttc ctg gag ctc aag cag aag cag gcc aac ctc gtg ctg    5232
Leu Gln Pro Phe Leu Glu Leu Lys Gln Lys Gln Ala Asn Leu Val Leu
    275                 280                 285 aag atc atc gag cag ctg ccc tcc gcc aag gaa tcc ccg gac aag ttc    5280
Lys Ile Ile Glu Gln Leu Pro Ser Ala Lys Glu Ser Pro Asp Lys Phe
290                 295                 300                 305 ctg gag gtg tgc acc tgg gtg gac cag atc gcc gct ctg aac gac tcc    5328
Leu Glu Val Cys Thr Trp Val Asp Gln Ile Ala Ala Leu Asn Asp Ser
                310                 315                 320 aag acc cgc aag acc act tcc gag acc gtc cgc gcc gtt cta gac agt    5376
Lys Thr Arg Lys Thr Thr Ser Glu Thr Val Arg Ala Val Leu Asp Ser
            325                 330                 335 ctc tcc gag aag aag aag tcg tcc ccc tagcatgccg ttcaaacatt          5423
Leu Ser Glu Lys Lys Lys Ser Ser Pro
            340                 345 tggcaataaa gtttcttaag attgaatcct gttgccggtc ttgcgatgat tatcatataa  5483
tttctgttga attacgttaa gcatgtaata attaacatgt aatgcatgac gttatttatg  5543
agatgggttt ttatgattag agtcccgcaa ttatacattt aatacgcgat agaaaacaaa  5603
atatagcgcg caaactagga taaattatcg cgcgcggtgt catctatgtt actagatcgg  5663
gcccgggaat aaaatatctt tatttttcatt acatctgtgt gttggttttt tgtgtgaatc  5723
gatagtacta acatacgctc tccatcaaaa caaaacgaaa caaaacaaac tagcaaaata  5783
ggctgtcccc agtgcaagtg caggtgccag aacatttcgg taccgagctc gaattcactg  5843
gccgtcgttt tacaacgtcg tgactgggaa accctggcg ttacccaact taatcgcctt   5903
gcagcacatc ccccttttcgc cagctggcgt aatagcgaag aggcccgcac cgatcgccct  5963
tcccaacagt tgcgcagcct gaatggcgaa tggcgcctga tcggtatttt ctccttacg   6023 catctgtgcg gtattttcaca ccgcatatgg tgcactctca gtacaatctg ctctgatgcc  6083
gcatagttaa gccagccccg acacccgcca cacccgctg acgcgccctg acgggcttgt    6143
ctgctcccgg catccgctta cagacaagct gtgaccgtct ccgggagctg catgtgtcag   6203
aggttttcac cgtcatcacc gaaacgcgcg a                                 6234

<210> SEQ ID NO 5
<211> LENGTH: 173
<212> TYPE: PRT
```

-continued

<213> ORGANISM: Artificial
<220> FEATURE:
<223> OTHER INFORMATION: Synthetic Construct

<400> SEQUENCE: 5

Met Ala Pro Lys Lys Arg Lys Val His Met Asn Thr Lys Tyr Asn
1               5                   10                  15

Lys Lys Phe Leu Leu Tyr Leu Ala Gly Phe Val Asp Gly Asp Gly Ser
            20                  25                  30

Ile Ile Ala Ser Ile Ser Pro Asn Gln Ser Arg Lys Phe Lys His Gln
        35                  40                  45

Leu Arg Leu Thr Phe Thr Val Thr Gln Lys Thr Gln Arg Arg Trp Phe
50                  55                  60

Leu Asp Lys Leu Val Asp Lys Ile Gly Val Gly Lys Val Arg Asp Arg
65                  70                  75                  80

Gly Ser Val Ser Asp Tyr Arg Leu Ser Gln Ile Lys Pro Leu His Asn
                85                  90                  95

Phe Leu Thr Gln Leu Gln Pro Phe Leu Lys Leu Lys Gln Lys Gln Ala
                100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160

Val Leu Asp Ser Leu Ser Glu Lys Lys Lys Ser Ser Pro
                165                 170

<210> SEQ ID NO 6
<211> LENGTH: 173
<212> TYPE: PRT
<213> ORGANISM: Artificial
<220> FEATURE:
<223> OTHER INFORMATION: Synthetic Construct

<400> SEQUENCE: 6

Met Ala Pro Lys Lys Arg Lys Val His Met Asn Thr Lys Tyr Asn
1               5                   10                  15

Glu Glu Phe Leu Leu Tyr Leu Ala Gly Phe Val Asp Gly Asp Gly Ser
            20                  25                  30

Ile Ile Ala Ser Ile Ser Pro Arg Gln Ser Tyr Lys Phe Lys His Glu
        35                  40                  45

Leu Arg Leu Thr Phe Gln Val Thr Gln Lys Thr Gln Arg Arg Trp Phe
50                  55                  60

Leu Asp Glu Leu Val Asp Glu Ile Gly Val Gly Lys Val Arg Asp Arg
65                  70                  75                  80

Gly Ser Val Ser Asp Tyr Arg Leu Ser Gln Ile Lys Pro Leu His Asn
                85                  90                  95

Phe Leu Thr Gln Leu Gln Pro Phe Leu Glu Leu Lys Gln Lys Gln Ala
                100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160

-continued

Val Leu Asp Ser Leu Ser Glu Lys Lys Lys Ser Ser Pro
            165                 170

<210> SEQ ID NO 7
<211> LENGTH: 68
<212> TYPE: DNA
<213> ORGANISM: Artificial
<220> FEATURE:
<223> OTHER INFORMATION: PCR amplicon of bar coding region around the
      BAY 39/40 recognition site (control)

<400> SEQUENCE: 7
cggtcaactt ccgtaccgag ccgcaggaac cgcaggagtg gacggacgac ctcgtccgtc    60
tgcgggac                                                              68

<210> SEQ ID NO 8
<211> LENGTH: 68
<212> TYPE: DNA
<213> ORGANISM: Artificial
<220> FEATURE:
<223> OTHER INFORMATION: PCR amplicon of bar coding region around the
      BAY 39/40 recognition site (PPT tolerant plant line1)

<400> SEQUENCE: 8
cggtcaactt ccgtaccgag ccgcaggaac cgcaggagtg gacggacgac ctcgtccgtc    60
tgcgggac                                                              68

<210> SEQ ID NO 9
<211> LENGTH: 67
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 1)

<400> SEQUENCE: 9
cggtcaactt ccgtaccgag ccgcaggaac cgcaggagtg gacgacgacc tcgtccgtct    60
gcgggac                                                               67

<210> SEQ ID NO 10
<211> LENGTH: 27
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 2)

<400> SEQUENCE: 10
cggtcaactt ccgtccgtct gcgggac                                         27

<210> SEQ ID NO 11
<211> LENGTH: 61
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 3)

<400> SEQUENCE: 11
cggtcaactt ccgtaccgag ccgcaggaac cgcaggagtg gacctcgtcc gtctgcggga    60
c                                                                     61

<210> SEQ ID NO 12
<211> LENGTH: 49

```
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 4)

<400> SEQUENCE: 12
cggtcaactt ccgtaccgag ccgcaggaac cctcgtccgt ctgcgggac                49

<210> SEQ ID NO 13
<211> LENGTH: 48
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 5)

<400> SEQUENCE: 13
cggtcaactt ccgtaccgag ccgcaggaac ctcgtccgtc tgcgggac                 48

<210> SEQ ID NO 14
<211> LENGTH: 56
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 6)

<400> SEQUENCE: 14
cggtcaactt ccgtaccgag ccgcaggaac cgcacgacct cgtccgtctg cgggac        56

<210> SEQ ID NO 15
<211> LENGTH: 68
<212> TYPE: DNA
<213> ORGANISM: Artificial
<220> FEATURE:
<223> OTHER INFORMATION: PCR amplicon of bar coding region around the
      BAY 39/40 recognition site (PPT sensitive  plant line1 7)

<400> SEQUENCE: 15
cggtcaactt ccgtaccgag ccgcaggaac cgcaggagtg gacggacgac ctcgtccgtc    60
tgcgggac                                                             68

<210> SEQ ID NO 16
<211> LENGTH: 163
<212> TYPE: PRT
<213> ORGANISM: Artificial
<220> FEATURE:
<223> OTHER INFORMATION: I-CreI

<400> SEQUENCE: 16

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Glu Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95
```

| Leu | Lys | Gln | Lys | Gln | Ala | Asn | Leu | Val | Leu | Lys | Ile | Ile | Glu | Gln | Leu |
|-----|-----|-----|-----|-----|-----|-----|-----|-----|-----|-----|-----|-----|-----|-----|-----|
|     |     |     | 100 |     |     |     | 105 |     |     |     | 110 |     |     |     |     |

| Pro | Ser | Ala | Lys | Glu | Ser | Pro | Asp | Lys | Phe | Leu | Glu | Val | Cys | Thr | Trp |
|-----|-----|-----|-----|-----|-----|-----|-----|-----|-----|-----|-----|-----|-----|-----|-----|
|     | 115 |     |     |     |     | 120 |     |     |     |     | 125 |     |     |     |     |

| Val | Asp | Gln | Ile | Ala | Ala | Leu | Asn | Asp | Ser | Lys | Thr | Arg | Lys | Thr | Thr |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Ser | Glu | Thr | Val | Arg | Ala | Val | Leu | Asp | Ser | Leu | Ser | Glu | Lys | Lys | Lys |
|-----|-----|-----|-----|-----|-----|-----|-----|-----|-----|-----|-----|-----|-----|-----|-----|
| 145 |     |     |     | 150 |     |     |     |     | 155 |     |     |     |     | 160 |     |

Ser Ser Pro

<210> SEQ ID NO 17
<211> LENGTH: 4925
<212> TYPE: DNA
<213> ORGANISM: Artificial Sequence
<220> FEATURE:
<223> OTHER INFORMATION: vector
<220> FEATURE:
<221> NAME/KEY: CDS
<222> LOCATION: (1267)..(1605)
<220> FEATURE:
<221> NAME/KEY: CDS
<222> LOCATION: (1795)..(2541)

<400> SEQUENCE: 17

```
ctaaattgta agcgttaata ttttgttaaa attcgcgtta aattttgtt aaatcagctc      60
attttttaac caataggccg aaatcggcaa atcccttat aaatcaaaag aatagaccga     120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacaccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtacggc    660
cgtcaaggcc aagcttcccg tgggggatcc accatacatg gagtcaaaaa ttcagatcga    720
ggatctaaca gaactcgccg tgaagactgg cgaacagttc atacagagtc ttttacgact    780
caatgacaag aagaaaatct tcgtcaacat ggtggagcac gacactctcg tctactccaa    840
gaatatcaaa gatacagtct cagaagacca aagggctatt gagactttc aacaaagggt    900
aatatcggga aacctcctcg gattccattg cccagctatc tgtcacttca tcaaaaggac    960
agtagaaaag gaaggtggca cctacaaatg ccatcattgc gataaaggaa aggctatcgt    1020
tcaagatgcc tctgccgaca gtggtcccaa agatggaccc ccacccacga ggagcatcgt    1080
ggaaaaagaa gacgttccaa ccacgtcttc aaagcaagtg gattgatgtg atatctccac    1140
tgacgtaagg gatgacgcac aatcccacta tccttcgcaa gacccttcct ctatataagg    1200
aagttcattt catttggaga ggactcgaga attaagcaaa agaagaagaa gaagaagtcc    1260
aaaacc atg gct aaa ccg cct aag aaa aag cgg aag gtt cat atg aat    1308
       Met Ala Lys Pro Pro Lys Lys Lys Arg Lys Val His Met Asn
         1               5                  10
acc aaa tac aac aaa gaa ttc ctt ctc tac cta gct ggt ttc gta gac    1356
Thr Lys Tyr Asn Lys Glu Phe Leu Leu Tyr Leu Ala Gly Phe Val Asp
 15              20                  25                  30
```

```
gga gat gga tct att atc gca tca att agc cct cgg caa tcg tac aaa    1404
Gly Asp Gly Ser Ile Ile Ala Ser Ile Ser Pro Arg Gln Ser Tyr Lys
             35                  40                  45 ttc aag cat gaa ctg cga ctt act ttc caa gtg aca cag aaa acc caa    1452
Phe Lys His Glu Leu Arg Leu Thr Phe Gln Val Thr Gln Lys Thr Gln
         50                  55                  60 agg aga tgg ttc ctt gat aaa ctc gtg gac gaa atc ggc gtt gga aag    1500
Arg Arg Trp Phe Leu Asp Lys Leu Val Asp Glu Ile Gly Val Gly Lys
         65                  70                  75 gtc aga gat aga ggg tcg gtg tcc gac tat agg ctc agt cag att aaa    1548
Val Arg Asp Arg Gly Ser Val Ser Asp Tyr Arg Leu Ser Gln Ile Lys
     80                  85                  90 cct ttg cat aac ttc cta act caa ctt caa cca ttt ctg aaa ttg aag    1596
Pro Leu His Asn Phe Leu Thr Gln Leu Gln Pro Phe Leu Lys Leu Lys
95                 100                 105                 110 cag aag cag gtaagtttct gcttctacct tgatatata tataataatt             1645
Gln Lys Gln atcattaatt agtagtaata taatatttca aatattttt tcaaaataaa agaatgtagt    1705
atatagcaat tgcttttctg tagtttataa gtgtgtatat tttaatttat aacttttcta   1765
atatatgacc aaaacatggt gatgtgcag gca aat ctg gtt ctc aag ata ata    1818
                                Ala Asn Leu Val Leu Lys Ile Ile
                                            115                 120 gag caa cta cca agc gca aag gaa tct cca gac aag ttt ttg gaa gtg    1866
Glu Gln Leu Pro Ser Ala Lys Glu Ser Pro Asp Lys Phe Leu Glu Val
             125                 130                 135 tgt acc tgg gtt gac caa atc gca gct ttg aat gat tcc aag aca cga    1914
Cys Thr Trp Val Asp Gln Ile Ala Ala Leu Asn Asp Ser Lys Thr Arg
         140                 145                 150 aag aca act tct gag act gtg aga gca gtc ctt gat tca tta ccc ggt    1962
Lys Thr Thr Ser Glu Thr Val Arg Ala Val Leu Asp Ser Leu Pro Gly
         155                 160                 165 tcg gtt ggt ggc tta agc cct agt cag gct agt tct gcc gct agt tct    2010
Ser Val Gly Gly Leu Ser Pro Ser Gln Ala Ser Ser Ala Ala Ser Ser
170                 175                 180                 185 gcc tca agc tct cca ggt tct ggg ata tcc gaa gcc ctt aga gct ggt    2058
Ala Ser Ser Ser Pro Gly Ser Gly Ile Ser Glu Ala Leu Arg Ala Gly
             190                 195                 200 gct act aag agc aag gag ttt ctc ctg tat tta gcc gga ttt gtt gat    2106
Ala Thr Lys Ser Lys Glu Phe Leu Leu Tyr Leu Ala Gly Phe Val Asp
         205                 210                 215 ggg gat ggt tca atc att gcc tct atc tca cca aat cag agc cgt aag    2154
Gly Asp Gly Ser Ile Ile Ala Ser Ile Ser Pro Asn Gln Ser Arg Lys
         220                 225                 230 ttt aag cac caa ctg agg ttg aca ttc acc gtg aca cag aag act caa    2202
Phe Lys His Gln Leu Arg Leu Thr Phe Thr Val Thr Gln Lys Thr Gln
         235                 240                 245 aga aga tgg ttt ctg gat aag ctt gtc gat gaa att ggc gtg gga aag    2250
Arg Arg Trp Phe Leu Asp Lys Leu Val Asp Glu Ile Gly Val Gly Lys
250                 255                 260                 265 gtt cgt gat aga gga tct gtt agt gac tat cgc cta tcc cag att aaa    2298
Val Arg Asp Arg Gly Ser Val Ser Asp Tyr Arg Leu Ser Gln Ile Lys
                 270                 275                 280 cct ctt cac aac ttc ctg acc cag ctt caa cct ttc ttg aaa tta aag    2346
Pro Leu His Asn Phe Leu Thr Gln Leu Gln Pro Phe Leu Lys Leu Lys
             285                 290                 295 cag aag cag gct aac ctg gtt ctc aaa atc att gag caa ctc cca tca    2394
Gln Lys Gln Ala Asn Leu Val Leu Lys Ile Ile Glu Gln Leu Pro Ser
         300                 305                 310
```

| | | | | | | | | | | | | | | | | |
|---|---|---|---|---|---|---|---|---|---|---|---|---|---|---|---|---|
| gca | aaa | gaa | tca | ccg | gat | aaa | ttt | ctg | gag | gta | tgc | act | tgg | gta | gac | 2442 |
| Ala | Lys | Glu | Ser | Pro | Asp | Lys | Phe | Leu | Glu | Val | Cys | Thr | Trp | Val | Asp | |
| | 315 | | | | 320 | | | | | 325 | | | | | | |

| | | | | | | | | | | | | | | | | |
|---|---|---|---|---|---|---|---|---|---|---|---|---|---|---|---|---|
| caa | att | gct | gct | ctg | aac | gat | tca | aag | act | cga | aaa | acc | act | agt | gag | 2490 |
| Gln | Ile | Ala | Ala | Leu | Asn | Asp | Ser | Lys | Thr | Arg | Lys | Thr | Thr | Ser | Glu | |
| 330 | | | | | 335 | | | | | 340 | | | | | 345 | |

| | | | | | | | | | | | | | | | | |
|---|---|---|---|---|---|---|---|---|---|---|---|---|---|---|---|---|
| aca | gtt | cgt | gct | gtc | tta | gat | tcc | ttg | tcc | gag | aaa | aag | aaa | agc | tct | 2538 |
| Thr | Val | Arg | Ala | Val | Leu | Asp | Ser | Leu | Ser | Glu | Lys | Lys | Lys | Ser | Ser | |
| | | | | 350 | | | | | 355 | | | | | 360 | | | ccc tgattcccag ataagggaat tagggttcct atagggtttc gctcatgtgt 2591
Pro tgagcatata agaaacccttt agtatgtatt tgtatttgta aatacttct atcaataaaa 2651 tttctaattc ctaaaaccaa aatccagcct gcaggtctag ataagtggga tatcacgtga 2711 agcttgcaag ctccagcttt tgttcccttt agtgagggtt aattgcgcgc ttggcgtaat 2771 catggtcata gctgtttcct gtgtgaaatt gttatccgct cacaattcca cacaacatac 2831 gagccggaag cataaagtgt aaagcctggg gtgcctaatg agtgagctaa ctcacattaa 2891 ttgcgttgcg ctcactgccc gctttccagt cgggaaacct gtcgtgccag ctgcattaat 2951 gaatcggcca acgcgcgggg agaggcggtt tgcgtattgg gcgctcttcc gcttcctcgc 3011 tcactgactc gctgcgctcg tcgttcggc tgcggcgagc ggtatcagct cactcaaagg 3071 cggtaatacg gttatccaca gaatcagggg ataacgcagg aaagaacatg tgagcaaaag 3131 gccagcaaaa ggccaggaac cgtaaaaagg ccgcgttgct ggcgtttttc cataggctcc 3191 gcccccctga cgagcatcac aaaaatcgac gctcaagtca gaggtggcga acccgacag 3251 gactataaag ataccaggcg tttccccctg gaagctccct cgtgcgctct cctgttccga 3311 ccctgccgct taccggatac ctgtccgcct ttctcccttc gggaagcgtg gcgctttctc 3371 atagctcacg ctgtaggtat ctcagttcgg tgtaggtcgt tcgctccaag ctgggctgtg 3431 tgcacgaacc ccccgttcag cccgaccgct gcgccttatc cggtaactat cgtcttgagt 3491 ccaacccggt aagacacgac ttatcgccac tggcagcagc cactggtaac aggattagca 3551 gagcgaggta tgtaggcggt gctacagagt tcttgaagtg gtggcctaac tacggctaca 3611 ctagaaggac agtatttggt atctgcgctc tgctgaagcc agttaccttc ggaaaaagag 3671 ttggtagctc ttgatccggc aaacaaacca ccgctggtag cggtggtttt tttgtttgca 3731 agcagcagat tacgcgcaga aaaaaaggat ctcaagaaga tcctttgatc ttttctacgg 3791 ggtctgacgc tcagtggaac gaaaactcac gttaagggat tttggtcatg agattatcaa 3851 aaaggatctt cacctagatc cttttaaatt aaaaatgaag ttttaaatca atctaaagta 3911 tatatgagta aacttggtct gacagttacc aatgcttaat cagtgaggca cctatctcag 3971 cgatctgtct atttcgttca tccatagttg cctgactccc cgtcgtgtag ataactacga 4031 tacgggaggg cttaccatct ggccccagtg ctgcaatgat accgcgagat ccacgctcac 4091 cggctccaga tttatcagca ataaaccagc cagccggaag ggccgagcgc agaagtggtc 4151 ctgcaacttt atccgcctcc atccagtcta ttaattgttg ccgggaagct agagtaagta 4211 gttcgccagt taatagtttg cgcaacgttg ttgccattgc tacaggcatc gtggtgtcac 4271 gctcgtcgtt tggtatggct tcattcagct ccggttccca acgatcaagg cgagttacat 4331 gatccccat gttgtgcaaa aaagcggtta gctccttcgg tcctccgatc gttgtcagaa 4391 gtaagttggc cgcagtgtta tcactcatgg ttatggcagc actgcataat tctcttactg 4451 tcatgccatc cgtaagatgc ttttctgtga ctggtgagta ctcaaccaag tcattctgag 4511

```
aatagtgtat gcggcgaccg agttgctctt gcccggcgtc aatacgggat aataccgcgc    4571
cacatagcag aactttaaaa gtgctcatca ttggaaaacg ttcttcgggg cgaaaactct    4631
caaggatctt accgctgttg agatccagtt cgatgtaacc cactcgtgca cccaactgat    4691
cttcagcatc ttttactttc accagcgttt ctgggtgagc aaaaacagga aggcaaaatg    4751
ccgcaaaaaa gggaataagg gcgacacgga aatgttgaat actcatactc ttcctttttc    4811
aatattattg aagcatttat cagggttatt gtctcatgag cggatacata tttgaatgta    4871
tttagaaaaa taaacaaata ggggttccgc gcacatttcc ccgaaaagtg ccac           4925
```

<210> SEQ ID NO 18
<211> LENGTH: 362
<212> TYPE: PRT
<213> ORGANISM: Artificial Sequence
<220> FEATURE:
<223> OTHER INFORMATION: Synthetic Construct

<400> SEQUENCE: 18

```
Met Ala Lys Pro Pro Lys Lys Arg Lys Val His Met Asn Thr Lys
1               5                   10                  15

Tyr Asn Lys Glu Phe Leu Leu Tyr Leu Ala Gly Phe Val Asp Gly Asp
            20                  25                  30

Gly Ser Ile Ile Ala Ser Ile Ser Pro Arg Gln Ser Tyr Lys Phe Lys
        35                  40                  45

His Glu Leu Arg Leu Thr Phe Gln Val Thr Gln Lys Thr Gln Arg Arg
    50                  55                  60

Trp Phe Leu Asp Lys Leu Val Asp Glu Ile Gly Val Gly Lys Val Arg
65                  70                  75                  80

Asp Arg Gly Ser Val Ser Asp Tyr Arg Leu Ser Gln Ile Lys Pro Leu
                85                  90                  95

His Asn Phe Leu Thr Gln Leu Gln Pro Phe Leu Lys Leu Lys Gln Lys
            100                 105                 110

Gln Ala Asn Leu Val Leu Lys Ile Ile Glu Gln Leu Pro Ser Ala Lys
        115                 120                 125

Glu Ser Pro Asp Lys Phe Leu Glu Val Cys Thr Trp Val Asp Gln Ile
    130                 135                 140

Ala Ala Leu Asn Asp Ser Lys Thr Arg Lys Thr Thr Ser Glu Thr Val
145                 150                 155                 160

Arg Ala Val Leu Asp Ser Leu Pro Gly Ser Val Gly Gly Leu Ser Pro
                165                 170                 175

Ser Gln Ala Ser Ser Ala Ala Ser Ser Ala Ser Ser Pro Gly Ser
            180                 185                 190

Gly Ile Ser Glu Ala Leu Arg Ala Gly Ala Thr Lys Ser Lys Glu Phe
        195                 200                 205

Leu Leu Tyr Leu Ala Gly Phe Val Asp Gly Asp Gly Ser Ile Ile Ala
    210                 215                 220

Ser Ile Ser Pro Asn Gln Ser Arg Lys Phe Lys His Gln Leu Arg Leu
225                 230                 235                 240

Thr Phe Thr Val Thr Gln Lys Thr Gln Arg Arg Trp Phe Leu Asp Lys
                245                 250                 255

Leu Val Asp Glu Ile Gly Val Gly Lys Val Arg Asp Arg Gly Ser Val
            260                 265                 270

Ser Asp Tyr Arg Leu Ser Gln Ile Lys Pro Leu His Asn Phe Leu Thr
        275                 280                 285
```

-continued

```
Gln Leu Gln Pro Phe Leu Lys Leu Lys Gln Lys Gln Ala Asn Leu Val
    290             295             300

Leu Lys Ile Ile Glu Gln Leu Pro Ser Ala Lys Glu Ser Pro Asp Lys
305             310             315                 320

Phe Leu Glu Val Cys Thr Trp Val Asp Gln Ile Ala Ala Leu Asn Asp
                325             330             335

Ser Lys Thr Arg Lys Thr Thr Ser Glu Thr Val Arg Ala Val Leu Asp
            340             345             350

Ser Leu Ser Glu Lys Lys Lys Ser Ser Pro
    355             360
```